United States Patent [19]

Inouye et al.

US005714575A

[11] Patent Number: 5,714,575
[45] Date of Patent: Feb. 3, 1998

[54] NUCLEIC ACIDS SEQUENCE, STRESS-INDUCED PROTEINS AND USES THEREOF

[75] Inventors: Masayori Inouye, Bridgewater; Pamela Jones, Edison; Jean-Pierre Etchegaray, Piscataway; Weining Jiang, Edison, all of N.J.; N. Stephen Pollitt, Los Altos, Calif.; Joel Goldstein, North Brunswick, N.J.

[73] Assignee: The University of Medicine and Dentistry of New Jersey, Newark, N.J.

[21] Appl. No.: 203,806

[22] Filed: Mar. 1, 1994

Related U.S. Application Data

[63] Continuation-in-part of Ser. No. 852,013, Mar. 9, 1992, abandoned, which is a continuation of Ser. No. 310,332, Feb. 13, 1989, abandoned.

[51] Int. Cl.$^6$ .................................................. C07K 14/24
[52] U.S. Cl. .................................................. 530/300
[58] Field of Search ................................. 530/300, 350, 530/358

[56] References Cited

PUBLICATIONS

Willimsky et al. 1992. J. Bacteriol. 174:6326–6335.
Sakura et al. 1988 Gene 73:499–507.
Tafuri et al 1990 P.N.A.S. 87:9028–9032.
Av–Gay et al. 1992 Nucleic Acids Res. 20, p. 5478.
Murray et al. 1992 PNAS 89:11–15.
Didier et al. 1988 PNAS 85:7322–7326.
Wistow et 1990 Nature 344:823–824.
Schuchel et al 1993 Nature 364:169–171.
Schroder et al 1993 Gene 136:277–280.
Goldstein et al. 1990 P.N.A.S. 87:283–.

*Primary Examiner*—Van Jagannathan
*Assistant Examiner*—K. Cochrane Carlson
*Attorney, Agent, or Firm*—Weiser & Associates, P.C.

[57] ABSTRACT

A family of stimuli-induced in particular stress or cold-shock induced genes and proteins are disclosed which have conserved amino acid domains. Nucleic acid sequences of the genes and the promoters are also described. Various utilities of the promoters and of the proteins are disclosed.

3 Claims, 19 Drawing Sheets

```
AGCTTTAATATAGCTCATGAAAGGTAAACATTGGCAGCTGAAGGGCCACGCAGACCATTT 60

ATCCGGCAAAATTCCACGCGTAATCCGGTGGTAATTTCTTCTGCATCGCGGAGATTGAGC 120

GCTGAAACATGAAGCTGGACATCGATACGACCATCGGATGGGGTGATAAGACCCTTGCCG 180

CTTTTGCCGTCAAAGGTTTTGACAATTCCTGTCATTTTACGGGACAAAAAAATTCCTTAA 240

-35                -10
TACTGATAACTTGGCGCACTATACACACGTTCCTGAAGAAAGCTATAGTTTTTTGATGGG 300
3 TRANSCRIPTION START SITES
                                  -35                -10
GTTGAAGATGGCTGGATGTCTAAAATAAACATTGCTTCATATGTTCAACTATGCGTTAAT 360
                                                           COLD-SHOCK INDUCIBLE
GATTGCGTCGGTTTGAAGAACAGACGATATACGAAGTAGTTTACTAAACGAGTTCTCATT 420

TCAGGTGTTATTCACTTATTCCTTCTTTGAGTCTCTCCAATAAAGTACGAAGTCGTTTCT 480

GTTATGCAAACCATTTATGCCGAAAGGCTCAAGTTAAGGAATGTAGA ATGTCAAATAAA 539
                                                MetSerAsnLys

ATGACTGGTTTAGTAAAATGGTTTAACGCTGATAAAGTTTTCGGCTTTATTTCTCCTGTT 599
MetThrGlyLeuValLysTrpPheAsnAlaAspLysGlyPheGlyPheIleSerProVal

GATGGTAGTAAAGATGTGTTTGTGCATTTTTCTGCGATTCAGAATGATAATTATCGAACC 659
AspGlySerLysAspValPheValHisPheSerAlaIleGlnAsnAspAsnTyrArgThr

TTATTTGAAGGTCAAAAGGTTACCTTCTCTATAGAGAGTGGTGCTAAAGGTCCTGCAGCA 719
LeuPheGluGlyGlnLysValThrPheSerIleGluSerGlyAlaLysGlyProAlaAla

GCAAATGTCATCATTACTGATTAA AATTCATCGCTCGTCTGTATACGATAACGAAGAAG 778
AlaAsnValIleIleThrAsp -

GCTGATGCCTGAGTAGAGATACGGACAGAGTAGTGAATATTGGATCTCTTTAATAAAAAG 838

TAAGGAGGTCCAATACATGAAACAATGGCTAGCATATTT 877
```

*FIG. 5*

```
CGGGATATCAGCAAAAGATATTTACCCCATTAATTTATTAGGATGTTTACATCGGATTTG 60
TGATTAAGCGTGGTATTATTTATTACGCGAAACGTTTCTCTCTTGAGGTTTTTGCTCATT 120
CATCAATTTTTCTTATTTTAAATTTACAATCCTTTGGGGATTGACTTCTCTTTAGGGTAA 180
TTAATAGCCGTTAACTGACTGTTTTATGAGAAAAAGTGATATAACTTTTTATTCATTGCA 240
TAGCAAAAAATGTGATATTGCACGCACTATGTAATAACTTCTCCCACTGGCCTGGAACAA 300
CTGAACTTATTGAACTATGTTAGAAAATACGCCAGTTTAAGTATCTGCCTGAACTGGCAA 360
GGTTAAGCACAATGATATATCGGCGCGTATTCCGTTGCATAAGTGTGCAAAAAAAGTGGA 420
AGACGTATCGAGATTTGTGCGTCTGATCGAGACATGTTTAAAAATGGCTTGCCATAATTA 480
ACGTTGTATGTGATAACAGATTTCGGGTTAAACGAGGTACAGTTCTGTTTATGTGTGGCA 540
TTTTCAGTAAAGAAGTCCTGAGTAAACACGTTGACGTTGAATACCGCTTCTCTGCCGAGC 600
CTTATATTGGTGCCTCATGCAGTAATGTGTCAGTTTTATCTATGTTATGCCTGCGGCGAA 660
GAAAACAATCTAAGGAATTTTTCAA  ATGGCAAAGATTAAAGGTCAGGTTAAGTGGTTC 718
                           MetAlaLysIleLysGlyGlnValLysTrpPhe
AACGAGTCTAAAGGTTTTGGCTTCATTACTCCGGCTGATGGCAGCAAAGATGTGTTCGTA 778
AsnGluSerLysGlyPheGlyPheIleThrProAlaAspGlySerLysAspValPheVal
CACTTCTCCGCTATCCAGGGTAATGGCTTAAAAACTCTGGCTGAAGGTCAGAACGTTGAG 838
HisPheSerAlaIleGlnGlyAsnGlyPheLysThrLeuAlaGluGlyGlnAsnValGlu
TTCGAAATTCAGGACGGCCAGAAAGGTCCGGCAGCTGTTAACGTAACAGCTATCTGA TC 897
PheGluIleGlnAspGlyGlnLysGlyProAlaAlaValAsnValThrAlaIle -
GAATCCACTGATCTGAAGTGTGAATACGCTTCAATCTCGCTATAAAGCCTCGTCGAATGC 957
GAGGCTTTTTACTATGCTTTATCTTCGCTCCTGGCGTTCGGATATTTGCCCGCCGCGTGA 1017
TTCGCGTTACACTTGCGGCCTTTAGTATCTGCCGGAGTTGTCATGTCTTTTTCCTGTCCA 1077
CTTTGCCATCAGCCTCTTTCGCGTGAAAAAAACAGCTATATCT 1120
```

FIG. 5A

```
              -35                           -10
cspA     TTGCAT  ◄── 17bp ──►  CTTAAT -35                           -10
cspB     TTGCTT  ◄── 17bp ──►  GTTAAT

CONSENSUS TRANSCRIPTION START SIGNAL:

TTGACA  ◄── 17bp ──►  TATAAT
```

*FIG. 7*

```
                           10         20         30
                            *          *          *
E. coli          CspA   MSGKMTGIVKWFNADKGFGFITPDDGSKDVFVHFSAI•••
E. coli          CspB   ••N••••L••••••••••••••••••S•V••••••••••
E. coli          CspC   •-A IK•Q•••••ES••••••••A•••••••••••••••
E. coli          CspD   •--EK•T••NA•••••C•EG•GE•IA•Y•T•••••••••
S. clavuligerus  SC7.0  •---A •T••••• E••••••AQ•G•GP•••Y•••••••
B. subtilis      CspB   •---LE•K••SE••••••••SE••••EV-E•QD•••••••
H. sapiens       YB1    IAT•VL•T•••VRN•Y•••NR••TKE••••••Q•T•

40         50         60         70
                  *          *          *          *
CspA    QNDG---Y-KSLDEGQKVSFTIESGAKGPAAGNVTSL
CspB    ••N----•-RT•F•••T•S••••••••A••IITD
CspC    •GN----F-T•A••N•E•EQD•Q•••••V•••AI
CspD    •M-----•-RT•KA•S•Q•DVHQ•P••NH•SVIVPVEVEAAVA
SC7.0   NAT•---F-R••E•N•V•N•DVTH•E-•Q•E•••SPA
CspB    •GE----F-T••E•••A•••E•VE•NR••Q•A••KEA
YB1     KKNNPRK•LR•VGD•ET••E•DVVE••EE•A••GP
```

FIG. 10

```
AGCTTTAATATAGCTCATGAAAGGTAAACATTGGCAGCTGAAGGGCCACGCAGACCATTT 60

ATCCGGCAAAATTCCACGCGTAATCCGGTGGTAATTTCTTCTGCATCGCGGAGATTGAGC 120

GCTGAAACATGAAGCTGGACATCGATACGACCATCGGATGGGGTGATAAGACCCTTGCCG 180

CTTTTGCCGTCAAAGGTTTTGACAATTCCTGTCATTTTACGGGACAAAAAAATTCCTTAA 240

TACTGATAACTTGGCGCACTATACACACGTTCCTGAAGAAAGCTATAGTTTTTTGATGGG 300

GTTGAAGATGGCTGGATGTCTAAAATAAACATTGCTTCATATGTTCAACTATGCGTTAAT 360

GATTGCGTCGGTTTGAAGAACAGACGATATACGAAGTAGTTTACTAAAGCAGTTCTCATT 420

TCAGGTGTTATACACTTATTCCTTCTTTGAGTCTCTCCAATTAAGTACGAAGTCGTTTCT 480

GTTATGCAAACCATTTATGCCGAAAGGCTCAAGTTAAGGAATGTAGA ATGTCAAATAAA 539
                                                 MetSerAsnLys

ATGACTGGTTTAGTAAAATGGTTTAACGCTGATAAAGGTTTCGGCTTTATTTCTCCTGTT 599
MetThrGlyLeuValLysTrpPheAsnAlaAspLysGlyPheGlyPheIleSerProVal

GATGGTAGTAAAGATGTGTTTGTGCATTTTPCTGCGATTCAGAATGATAATTATCGAACC 659
LeuPheGluGlyGlnLysValThrPheSerIleGluSerGlyAlaLysGlyProAlaAla

GCAATAGTCATCATTACTGATTAA AATTCATCGCTCGTCTGTATACGATAACGAAGAAG 778
AlaAsnValIleIleThrAsp -

GCTGATGCCTGAGTAGAGATACGGACAGAGTAGTGAATATTGGATCTCTTTAATAAAAAG 838

TAAGGAGGTCCAATACATGAAACAATGGCTAGCATATTT 877
```

FIG. 11

```
CGGGATATCAGCAAAAGATATTTACCCCATTAATTTATTAGGATGTTTACATCGGATTTG  60

TGATTAAGCGTGGTATTATTTATTACGCGAAACGTTTCTCTCTTGAGGTTTTTGCTCATT  120

CATCAATTTTTCTTATTTTAAATTTACAATCCTTTGGGGATTGACTTCTCTTTAGGGTAA  180

TTAATAGCCGTTAACTGACTGTTTTATGAGAAAAAGTGATATAACTTTTTATTCATTGCA  240

TAGCAAAAAATGTGATATTGCACGCACTATGTAATAACTTCTCCCACTGGCCTGGAACAA  300

CTGAACTAATTGAACTATGTTAGAAAATACGCCAGTTTAAGTATCTGCCTGAACTGGCAA  360

GGTTAAGCACAATGATATATCGGCGCGTATTCCGTTGCATAAGTGTGCAAAAAAGTGGA  420

AGACGTATCGAGATTTGTGCGTCTGATCGAGACATGTTTAAAAATGGCTTGCCATAATTA  480

ACGTTGTATGTGATAACAGATTTCGGGTTAAACGAGGTACAGTTCTGTTTATGTGTGGCA  540

TTTTCAGTAAAGAAGTCCTGAGTAAACACGTTGACGTTGAATACCGCTTCTCTGCCGAGC  600

CTTATATTGGTGCCTCATGCAGTAATGTGTCAGTGTTATCTATGTTATGCCTGCGGCGAA  660

GAAAACAATCTAAGGAATTTTTCAA  ATGGCAAAGATTAAAGGTCAGGTTAAGTGGTTC  718
                           MetAlaLysIleLysGlyGlnValLysTrpPhe

AACGAGTCTAAAGGTTTTGGCTTCATTACTCCGGCTGATGGCAGCAAAGATGTGTTCGTA  778
AsnGluSerLysGlyPheGlyPheIleThrProAlaAspGlySerLysAspValPheVal

CACTTCTCCGCTATCCAGGGTAATGGCTTCAAAACTCTGGCTGAAGGTCAGAACGTTGAG  838
HisPheSerAlaIleGlnGlyAsnGlyPheLysThrLeuAlaGluGlyGlnAsnValGlu

TTCGAAATTCAGGACGGCCAGAAAGGTCCGGCAGCTGTTAACGTAACAGCTATCTGA TC  897
PheGluIleGlnAspGlyGlnLysGlyProAlaAlaValAsnValThrAlaIle -

GAATCCACTGATCTGAAGTGTGAATACGCTTCAATCTCGCTATAAAGCCTCGTCGAATGC  957

GAGGCTTTTTACTATGCTTTATCTTCGCTCCTGGCGTTCGGATATTTGCCCGCCGCGTGA  1017

TTCGCGTTACACTTGCGGCCTTTAGTATCTGCCGGAGTTGTCATGTCTTTTTCCTGTCCA  1077

CTTTGCCATCAGCCTCTTTCGCGTGAAAAAAACAGCTATATCT  1120
```

FIG. 12

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 877 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 528..743

( x i ) SEQUENCE DESCRIPTION: SEQ ID NO:1:

```
AGCTTTAATA TAGCTCATGA AAGGTAAACA TTGGCAGCTG AAGGGCCACG CAGACCATTT       60

ATCCGGCAAA ATTCCACGCG TAATCCGGTG GTAATTTCTT CTGCATCGCG GAGATTGAGC      120

GCTGAAACAT GAAGCTGGAC ATCGATACGA CCATCGGATG GGTGATAAG ACCCTTGCCG       180

CTTTTGCCGT CAAAGGTTTT GACAATTCCT GTCATTTAC GGGACAAAAA AATTCCTTAA       240

TACTGATAAC TTGGCGCACT ATACACACGT TCCTGAAGAA AGCTATAGTT TTTTGATGGG      300

GTTGAAGATG GCTGGATGTC TAAAATAAAC ATTGCTTCAT ATGTTCAACT ATGCGTTAAT      360

GATTGCGTCG GTTTGAAGAA CAGACGATAT ACGAAGTAGT TTACTAAAGC AGTTCTCATT      420

TCAGGTGTTA TTCACTTATT CCTTCTTTGA GTCTCTCCAA TTAAGTACGA AGTCGTTTCT      480

GTTATGCAAA CCATTTATGC CGAAAGGCTC AAGTTAAGGA ATGTAGA ATG TCA AAT       536
                                                  Met Ser Asn
                                                    1

AAA ATG ACT GGT TTA GTA AAA TGG TTT AAC GCT GAT AAA GGT TTC GGC       584
Lys Met Thr Gly Leu Val Lys Trp Phe Asn Ala Asp Lys Gly Phe Gly
      5              10                 15

TTT ATT TCT CCT GTT GAT GGT AGT AAA GAT GTG TTT GTG CAT TTT TCT       632
Phe Ile Ser Pro Val Asp Gly Ser Lys Asp Val Phe Val His Phe Ser
 20             25                  30                       35

GCG ATT CAG AAT GAT AAT TAT CGA ACC TTA TTT GAA GGT CAA AAG GTT       680
Ala Ile Gln Asn Asp Asn Tyr Arg Thr Leu Phe Glu Gly Gln Lys Val
              40                  45                 50

ACC TTC TCT ATA GAG AGT GGT GCT AAA GGT CCT GCA GCA GCA AAT GTC       728
Thr Phe Ser Ile Glu Ser Gly Ala Lys Gly Pro Ala Ala Ala Asn Val
             55                 60                 65

ATC ATT ACT GAT TAAAATTCAT CGCTCGTCTG TATACGATAA CGAAGAAGGC           780
Ile Ile Thr Asp
            70

TGATGCCTGA GTAGAGATAC GGACAGAGTA GTGAATATTG GATCTCTTTA ATAAAAAGTA     840

AGGAGGTCCA ATACATGAAA CAATGGCTAG CATATTT                              877
```

( 2 ) INFORMATION FOR SEQ ID NO:2:

( i ) SEQUENCE CHARACTERISTICS:
        ( A ) LENGTH: 71 amino acids
        ( B ) TYPE: amino acid
        ( D ) TOPOLOGY: linear (ii) MOLECULE TYPE: protein (xi) SEQUENCE DESCRIPTION: SEQ ID NO:2:

```
Met Ser Asn Lys Met Thr Gly Leu Val Lys Trp Phe Asn Ala Asp Lys
 1               5                  10                  15

Gly Phe Gly Phe Ile Ser Pro Val Asp Gly Ser Lys Asp Val Phe Val
                20                  25                  30

His Phe Ser Ala Ile Gln Asn Asp Asn Tyr Arg Thr Leu Phe Glu Gly
            35                  40                  45

Gln Lys Val Thr Phe Ser Ile Glu Ser Gly Ala Lys Gly Pro Ala Ala
        50                  55                  60

Ala Asn Val Ile Ile Thr Asp
 65                  70
```

(2) INFORMATION FOR SEQ ID NO:3:

(i) SEQUENCE CHARACTERISTICS:
  (A) LENGTH: 1120 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 686..895

(xi) SEQUENCE DESCRIPTION: SEQ ID NO:3:

```
CGGGATATCA GCAAAAGATA TTTACCCCAT TAATTTATTA GGATGTTTAC ATCGGATTTG      60
TGATTAAGCG TGGTATTATT TATTACGCGA AACGTTTCTC TCTTGAGGTT TTTGCTCATT     120
CATCAATTTT TCTTATTTTA AATTTACAAT CCTTTGGGGA TTGACTTCTC TTTAGGGTAA     180
TTAATAGCCG TTAACTGACT GTTTTATGAG AAAAAGTGAT ATAACTTTTT ATTCATTGCA     240
TAGCAAAAAA TGTGATATTG CACGCACTAT GTAATAACTT CTCCCACTGG CCTGGAACAA     300
CTGAACTTAT TGAACTATGT TAGAAAATAC GCCAGTTTAA GTATCTGCCT GAACTGGCAA     360
GGTTAAGCAC AATGATATAT CGGCGCGTAT TCCGTTGCAT AAGTGTGCAA AAAAGTGGA     420
AGACGTATCG AGATTTGTGC GTCTGATCGA GACATGTTTA AAAATGGCTT GCCATAATTA     480
ACGTTGTATG TGATAACAGA TTTCGGGTTA AACGAGGTAC AGTTCTGTTT ATGTGTGGCA     540
TTTTCAGTAA AGAAGTCCTG AGTAAACACG TTGACGTTGA ATACCGCTTC TCTGCCGAGC     600
CTTATATTGG TGCCTCATGC AGTAATGTGT CAGTTTATC TATGTTATGC CTGCGGCGAA     660
GAAAACAATC TAAGGAATTT TTCAA ATG GCA AAG ATT AAA GGT CAG GTT AAG     712
                              Met Ala Lys Ile Lys Gly Gln Val Lys
                               1               5

TGG TTC AAC GAG TCT AAA GGT TTT GGC TTC ATT ACT CCG GCT GAT GGC     760
Trp Phe Asn Glu Ser Lys Gly Phe Gly Phe Ile Thr Pro Ala Asp Gly
 10                  15                  20                  25

AGC AAA GAT GTG TTC GTA CAC TTC TCC GCT ATC CAG GGT AAT GGC TTC     808
Ser Lys Asp Val Phe Val His Phe Ser Ala Ile Gln Gly Asn Gly Phe
                30                  35                  40

AAA ACT CTG GCT GAA GGT CAG AAC GTT GAG TTC GAA ATT CAG GAC GGC     856
Lys Thr Leu Ala Glu Gly Gln Asn Val Glu Phe Glu Ile Gln Asp Gly
            45                  50                  55

CAG AAA GGT CCG GCA GCT GTT AAC GTA ACA GCT ATC TGATCGAATC           902
Gln Lys Gly Pro Ala Ala Val Asn Val Thr Ala Ile
        60                  65                  70

CACTGATCTG AAGTGTGAAT ACGCTTCAAT CTCGCTATAA AGCCTCGTCG AATGCGAGGC     962
```

```
TTTTTACTAT  GCTTTATCTT  CGCTCCTGGC  GTTCGGATAT  TTGCCCGCCG  CGTGATTCGC    1022

GTTACACTTG  CGGCCTTTAG  TATCTGCCGG  AGTTGTCATG  TCTTTTTCCT  GTCCACTTTG    1082

CCATCAGCCT  CTTTCGCGTG  AAAAAAACAG  CTATATCT                              1120
```

(2) INFORMATION FOR SEQ ID NO:4:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Lys Ile Lys Gly Gln Val Lys Trp Phe Asn Glu Ser Lys Gly
 1               5                  10                  15

Phe Gly Phe Ile Thr Pro Ala Asp Gly Ser Lys Asp Val Phe Val His
            20                  25                  30

Phe Ser Ala Ile Gln Gly Asn Gly Phe Lys Thr Leu Ala Glu Gly Gln
        35                  40                  45

Asn Val Glu Phe Glu Ile Gln Asp Gly Gln Lys Gly Pro Ala Ala Val
    50                  55                  60

Asn Val Thr Ala Ile
65
```

(2) INFORMATION FOR SEQ ID NO:5:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:5:

```
AACGGUUUGA  CGUACAGACC  AUUAAAGCAG  UGUAGUAAGG  CAAGUCCCUU  CAAGAGUUAU    60

CGUUGAUACC  CCUCGUAGUG  CACAUUCCUU  UAACGCUUCA  AAAUCUGUAA  AGCACGCCAU   120

AUCGCCGAAA  GGCACACUUA  AUUAUUAAAG  GUAAUACACU                           160
```

(2) INFORMATION FOR SEQ ID NO:6:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

```
CGUCGGUUUG  AAGAACAGAC  GAUAUACGAA  GUAGUUUACU  AAAGCAGUUC  UCAUUUCAGG    60

UGUUAUUCAC  UUAUUCCUUC  UUUGAGUCUC  UCCAAUUAAG  UACGAAGUCG  UUUCUGUUAU   120

GCAAACCAUU  UAUGCCGAAA  GGCUCAAGUU  AAGGAAUGUA  GA                       162
```

(2) INFORMATION FOR SEQ ID NO:7:

(i) SEQUENCE CHARACTERISTICS:
        (A) LENGTH: 70 amino acids
        (B) TYPE: amino acid
        (D) TOPOLOGY: linear ( i i ) MOLECULE TYPE: protein ( v i ) ORIGINAL SOURCE:
    ( A ) ORGANISM: Escherichia coli.

( x i ) SEQUENCE DESCRIPTION: SEQ ID NO:7:

```
Met Ser Gly Lys Met Thr Gly Ile Val Lys Trp Phe Asn Ala Asp Lys
1               5                   10                  15
Gly Phe Gly Phe Ile Thr Pro Asp Asp Gly Ser Lys Asp Val Phe Val
            20                  25                  30
His Phe Ser Ala Ile Gln Asn Asp Gly Tyr Lys Ser Leu Asp Glu Gly
        35                  40                  45
Gln Lys Val Ser Phe Thr Ile Glu Ser Gly Ala Lys Gly Pro Ala Ala
    50                  55                  60
Gly Asn Val Thr Ser Leu
65              70
```

( 2 ) INFORMATION FOR SEQ ID NO:8:

( i ) SEQUENCE CHARACTERISTICS:
        ( A ) LENGTH: 71 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Escherichia coli ( x i ) SEQUENCE DESCRIPTION: SEQ ID NO:8:

```
Met Ser Asn Lys Met Thr Gly Leu Val Lys Trp Phe Asn Ala Asp Lys
1               5                   10                  15
Gly Phe Gly Phe Ile Ser Pro Val Asp Gly Ser Lys Asp Val Phe Val
            20                  25                  30
His Phe Ser Ala Ile Gln Asn Asp Asn Tyr Arg Thr Leu Phe Glu Gly
        35                  40                  45
Gln Lys Val Thr Phe Ser Ile Glu Ser Gly Ala Lys Gly Pro Ala Ala
    50                  55                  60
Ala Asn Val Ile Ile Thr Asp
65              70
```

( 2 ) INFORMATION FOR SEQ ID NO:9:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Escherichia coli ( x i ) SEQUENCE DESCRIPTION: SEQ ID NO:9:

```
Met Ala Lys Ile Lys Gly Gln Val Lys Trp Phe Asn Glu Ser Lys Gly
1               5                   10                  15
Phe Gly Phe Ile Thr Pro Ala Asp Gly Ser Lys Asp Val Phe Val His
            20                  25                  30
Phe Ser Ala Ile Gln Gly Asn Gly Phe Lys Thr Leu Ala Glu Gly Gln
        35                  40                  45
Asn Val Glu Phe Glu Ile Gln Asp Gly Gln Lys Gly Pro Ala Ala Val
    50                  55                  60
Asn Val Thr Ala Ile
```

( 2 ) INFORMATION FOR SEQ ID NO:10:

( i ) SEQUENCE CHARACTERISTICS:
        ( A ) LENGTH: 74 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Escherichia coli ( x i ) SEQUENCE DESCRIPTION: SEQ ID NO:10:

```
Met Glu Lys Gly Thr Val Lys Trp Phe Asn Asn Ala Lys Gly Phe Gly
 1               5                  10                  15

Phe Ile Cys Pro Glu Gly Gly Gly Glu Asp Ile Phe Ala His Tyr Ser
            20                  25                  30

Thr Ile Gln Met Asp Gly Tyr Arg Thr Leu Lys Ala Gly Gln Ser Val
        35                  40                  45

Gln Phe Asp Val His Gln Gly Pro Lys Gly Asn His Ala Ser Val Ile
    50                  55                  60

Val Pro Val Glu Val Glu Ala Ala Val Ala
65                  70
```

( 2 ) INFORMATION FOR SEQ ID NO:11:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Streptomyces clavuligerus ( x i ) SEQUENCE DESCRIPTION: SEQ ID NO:11:

```
Met Ala Thr Gly Thr Val Lys Trp Phe Asn Ala Glu Lys Gly Phe Gly
 1               5                  10                  15

Phe Ile Ala Gln Asp Gly Gly Gly Pro Asp Val Phe Val His Tyr Ser
            20                  25                  30

Ala Ile Asn Ala Thr Gly Phe Arg Ser Leu Glu Glu Asn Gln Val Val
        35                  40                  45

Asn Phe Asp Val Thr His Gly Glu Gly Pro Gln Ala Glu Asn Val Ser
    50                  55                  60

Pro Ala
65
```

( 2 ) INFORMATION FOR SEQ ID NO:12:

( i ) SEQUENCE CHARACTERISTICS:
        ( A ) LENGTH: 67 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacillus subtilis ( x i ) SEQUENCE DESCRIPTION: SEQ ID NO:12:

```
Met Leu Glu Gly Lys Val Lys Trp Phe Asn Ser Glu Lys Gly Phe Gly
 1               5                  10                  15
```

-continued

```
Phe Ile Glu Val Glu Gly Gln Asp Asp Val Phe Val His Phe Ser Ala
         20                  25                  30

Ile Gln Gly Glu Gly Phe Lys Thr Leu Glu Glu Gly Gln Ala Val Ser
         35                  40                  45

Phe Glu Ile Val Glu Gly Asn Arg Gly Pro Gln Ala Ala Asn Val Thr
         50                  55                  60

Lys Glu Ala
 65
```

( 2 ) INFORMATION FOR SEQ ID NO:13:

( i ) SEQUENCE CHARACTERISTICS:
        ( A ) LENGTH: 74 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:13:

```
Ile Ala Thr Lys Val Leu Gly Thr Val Lys Trp Phe Asn Val Arg Asn
 1            5                  10                  15

Gly Tyr Gly Phe Ile Asn Arg Asn Asp Thr Lys Glu Asp Val Phe Val
         20                  25                  30

His Gln Thr Ala Ile Lys Lys Asn Asn Pro Arg Lys Tyr Leu Arg Ser
         35                  40                  45

Val Gly Asp Gly Glu Thr Val Glu Phe Asp Val Val Glu Gly Glu Lys
         50                  55                  60

Gly Glu Glu Ala Ala Asn Val Thr Gly Pro
 65                  70
```

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:14:

```
Asp Gly Ser Lys
 1
```

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:15:

```
Tyr Arg Thr Leu
 1
```

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:16:

```
Thr Pro Asp Asp
 1
```

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:17:

Met Ser Gly Lys Met Thr
    1               5

(2) INFORMATION FOR SEQ ID NO:18:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:18:

Val Lys Trp Phe Asn
    1             5

NUCLEIC ACIDS SEQUENCE, STRESS-INDUCED PROTEINS AND USES THEREOF

RELATED CASE

This is a continuation-in-part application of pending parent application U.S. Ser. No. 07/852,013, filed Mar. 9, 1992, now abandoned, which is in turn a continuation of application Ser. No. 07/310,332, now abandoned, filed Feb. 13, 1989. That patent application (parent application) is incorporated herein by reference in its entirety.

Publications and manuscripts which are attached and co-filed herewith are also incorporated by reference in their entirety.

The parent application discloses cold-shock proteins which are induced by cold-shock following a shift to lower temperature from physiological growth temperatures. E. coli was shown to grow at low temperatures after cold-shock induction. Cold shock proteins are reported to be synthesized during a growth lag when the growth temperature for the bacteria is decreased from 37° to 10° C. Other features of these proteins and their promoters are disclosed in the parent application.

SUMMARY OF THE INVENTION

The present invention further describes these and other members of a family of stress-induced, in particular cold-shock induced proteins (Csp), their synthesis following a shift from physiological growth temperature of a microorganism to temperatures below physiological, nucleotide sequences of stress-induced and cold-shock genes, deduced amino acid sequences thereof and cold-shock induced and other promoters. The invention also describes the expression of proteins other than the cold-shock proteins under the direction of cold-shock promoters. Various utilities of the cold-shock proteins and promoters are described.

Methods, systems and compositions are provided for genetically transforming microorganisms, particulary bacteria, to produce genotypical capability, particularly to produce "cold-shock" or antifreeze" and other proteins. Also provided are segments of DNA ("promoter") that contain signals that direct the proper binding of the RNA polymerase holoenzyme and its subsequent activation to a form capable of initiating specific RNA transcription. The promoter which is described herein is cold-induced and capable of controlling the expression of the cspA gene which encodes a cold-shock or antifreeze or other proteins. Practical applications are referred to hereinafter.

Genetic systems are provided for expressing proteins called cold-shock or antifreeze proteins, particularly a cold-shock protein of E. coli designated cs7.4 or CspA.

The invention provides a novel polypeptide which is synthesized in E. coli in response to a decrease of the temperature below ambient, or physiological growth temperature. The polypeptide (or protein) is a 7.4 kdal protein induced under cold-shock and had been designated as "cs7.4".

A noteworthy aspect of the polypeptide is that it is stable at temperatures above the cold temperature at which it was induced.

The invention also provides the gene encoding the cs7.4 protein. The invention provides further the cold-induced promoter which controls the expression of the gene encoding cs7.4 and which promoter also is capable of initiating transcription of proteins other than cs7.4 in response to a shift in temperature below the microorganism growth temperatures.

The invention also provides a system for expressing the gene encoding the antifreeze protein under the direction of a promoter other than the promoter of the invention.

The invention further provides various DNA constructs, including cloning vectors, e.g., plasmids which contain the promoter, the structural gene and other necessary functional DNA elements, and transformed hosts.

The invention provides a cold-shock induced promoter (the "native" promoter) which is capable of regulating the expression of a cold-shock induced gene encoding an antifreeze protein.

The invention provides further a promoter ("native") which is capable of controlling the expression of a gene encoding an antifreeze protein or another protein at temperature below physiological temperatures. Although cs7.4 is frequently referred to herein, it is contemplated that any protein can be produced by the promoter of the invention.

The invention also provides for the expression of a gene encoding an antifreeze protein under the control of a heterologous (non-native) promoter at physiological temperatures.

The invention further contemplates that having further elucidated the promoter sequence, the DNA sequence of the promoter can be generated synthetically; such promoter will be useful to regulate the expression of proteins at low temperatures, i.e., temperatures below physiological temperature.

It is a noteworthy aspect of the invention that the promoter can be "uncoupled" in the sense that it can be used without the native structural gene and conversely, the structural gene can be controlled by a heterologous promoter.

Other aspects of the invention will become apparent from the description which follows.

The invention provides a method for producing a "cold-shock" protein, a promoter therefor and various constructs. In one embodiment that will be described hereinafter, the gene encoding the cold-shock protein is expressed under the regulation of a heterologous promoter. In another embodiment, the cold-shock induced promoter is used to control the synthesis of a heterologous protein in response to lowering of the growth temperature.

The method of the invention to induce and produce the cs7.4 protein of the invention comprises growing in a nutrient rich medium at an exponential rate an appropriate microorganism, for instance an E. coli, to a desired growth density at physiological growth temperature for the particular microorganism. For E. coli such temperature may be in the range of about 10° to about 50° C., preferably in the range of 20° to about 40° C. Each microorganism is known to have its optimum growth temperature; for E. coli raising the temperature above about 40° C. or lowering it below 20° C. results in progressively slower growth, until growth ceases, at the maximum temperature of growth, about 49° C., or the minimum, about 8° C.

When the desired degree of growth is attained (monitored by an appropriate method, such as spectrophotometrically), the temperature is rapidly shifted to a lower temperature about 10° and below about 20° C., preferably below about 15° C. and about 8° C. Lower temperatures generally do not sustain practical growth rates. If desirable, a shift to lower temperature but above the temperature at which no growth of the microorganism takes place may also be performed. The culture is grown in the lower temperature range for the appropriate period of time for optimum production of the polypeptide of the invention. The kinetics of polypeptide induction are followed by appropriate method such as pulse labeling with radioactive methionine, harvesting the culture, processing and separation by two-dimensional gel electrophoresis and determining by autoradiography the amount of protein synthesized.

It was found that the cs7.4 protein of the invention is not synthesized at physiological growth temperature at which the microorganism normally grows, in this case the *E. coli*; the polypeptide is synthesized in the lower temperature range. Sudden induction of the synthesis of the polypeptide takes place within approximately the first 30 minutes after temperature shift to 10° C. or 15° C. Maximal induction and rate of synthesis is temperature dependent after temperature shift. After shift to 15° C., maximal synthesis is attained at 30–60 minutes post temperature shift; maximal rate of synthesis is approximately 13.1% of total protein synthesis. Shift to 10° C. gives a maximal rate of the synthesis of approximately 8.5% of total protein synthesis at 60 to 90 minutes post-shift. Adjustment of the temperature therefore allows for adjusting the rate of synthesis and/or yield of the polypeptide as being suited for the objective of the invention. After the maximum total polypeptide yield has been reached, the rate of synthesis thereof drops off, ultimately reaching a fraction, e.g., about a fifth of the maximum in the case of the culture shifted to 15° C. and about three-fifths of the maximum in the case of the culture shifted to 10° C.

A noteworthy characteristic of the cs7.4 protein of the invention is its stability at temperatures above the temperature range at which it was induced and synthesized. Such physiological temperature may range from about above 15° C. to about 40° C., or higher. The protein is stable after synthesis at 15° C. for 20 hours, (only about 30% of the protein degraded), and stable at 37° C. (for at least 1.5 hours).

The invention further provides a cold-induced cytoplasmic protein, designated cs7.4, which is stable at growth temperature of a microorganism, e.g., *E. coli*. The polypeptide has the following partial amino acid sequence SGKMTG(X)VKWFNADKGFGFI wherein X is leucine or isoleucine, see Sequence ID No. 7. Both isoleucine and leucine have been identified (64% and 36%, respectively). Thus, the invention includes either and both polypeptides. The polypeptide of the invention is a 70 amino acid residue protein. The calculated molecular weight is 7402 daltons and the calculated pI is 5.92. The polypeptide is very hydrophilic, containing over 20% charged residues. Lysine residues make up 10% of the protein. No homology was detected with any other sequence in the NBRF data base.

The sequence contains an open reading frame beginning with an ATG codon at nucleotide 617 of the cloned HindIII fragment and extending for 270 nucleotides ending with a TAA termination codon. This open reading frame is the coding region of the gene herein designated cspA responsible for cs7.4 synthesis. The invention includes within its scope the nucleotide sequence or any partial sequence thereof which codes for the polypeptide cs7.4 or a polypeptide having the properties of cs7.4 (functional equivalent). The invention also includes any equivalent nucleotide sequence wherein one or more codons have been substituted by certain other codons, which equivalent nucleotide sequence codes for the cs7.4 polypeptide, or a functional equivalent thereof.

In the work in connection with this invention, some evidence was adduced that suggests to date that there may be two copies (cspA and cspB) of the gene encoding the cold-induced polypeptide cs7.4. The evidence is further discussed below. The invention includes within its scope such other possible gene which encodes the cs7.4 polypeptide or its functional equivalent.

In accordance with the invention, it is conceivable that from the 997 bp fragment of the cloned HindIII fragment, the cspA structural gene can be removed and be replaced by a foreign gene. If necessary, the inverted repeat at the 3' end at 857–866 and 869–878 may be conserved; but if not, the HindIII fragment would not need to contain the base pairs upstream of the TAA stop codon. The foreign gene (or part thereof) would be inducible by the cold-induced promoter (or its equivalent) and be capable of encoding a target protein.

In another embodiment of the invention the cold-shock protein would be expressed by the gene coding for it under the control of the promoter of the invention.

In yet another embodiment of the invention, a promoter other than the native promoter can regulate expression of the cs7.4 gene at physiological temperatures, i.e., within the temperature ranges at which bacteria exponentially grow. Thus, in accordance with the invention, a heterologous promoter, an *E. coli* lac promoter, has been used to regulate the expression of the cs7.4 gene. The cspA structural gene was subcloned into a high level expression vector, pINIII (lpp$^{P5}$) (7). The resulting construct is pJJG12. Upon addition of isopropylthiogalactoside (IPTG), expression of the cs7.4 protein at 37° C. was detected by SDS polyacrylamide gel electrophoresis of whole cell lysate. The expression of the protein was 5–10 fold less than that obtained from expression regulated by the native promoter at 15° C.

As the result of this teaching, one skilled in the art will appreciate that other suitable promoters other than the lac promoter, such as the trp, tac, promoter, lambda pL, ompF, opp, and other promoters may be used to regulate the expression of the gene coding for the desired protein. When other transformed microorganisms such as yeast are used to express the proteins, promoter like GAL10 and others may be suitable.

Furthermore, as described briefly above, the cspA promoter of the invention which is active at low temperatures, can be used to control the expression of a protein other than the cs7.4 cold-shock protein. Thus, this property opens up yet other possibilities.

These observations do not apply only to antifreeze proteins but to the expression of any proteins which heretofore could not be expressed in the desired conformation at physiological temperatures; these proteins, it can be visualized, could be expressed at lower, non-injurious temperatures with the assistance of the promoter of the invention.

BRIEF DESCRIPTION OF THE FIGURES

FIG. 5 shows the nucleotide sequence of CspB and the deduced amino acid sequence of CspB protein.

FIG. 5A shows the nucleotide sequence of CspC and its deduced amino acid sequence.

FIG. 7 shows the CspA leader region.

FIG. 10 shows a comparison of *E. coli* CspA with other CspA-like proteins.

FIG. 11 shows the nucleotide sequence and the deduced amino acid sequence of CspB.

FIG. 12 shows the nucleotide sequence and the deduced amino acid sequence of CspC.

DESCRIPTION OF THE PREFERRED EMBODIMENTS

Figure 1:
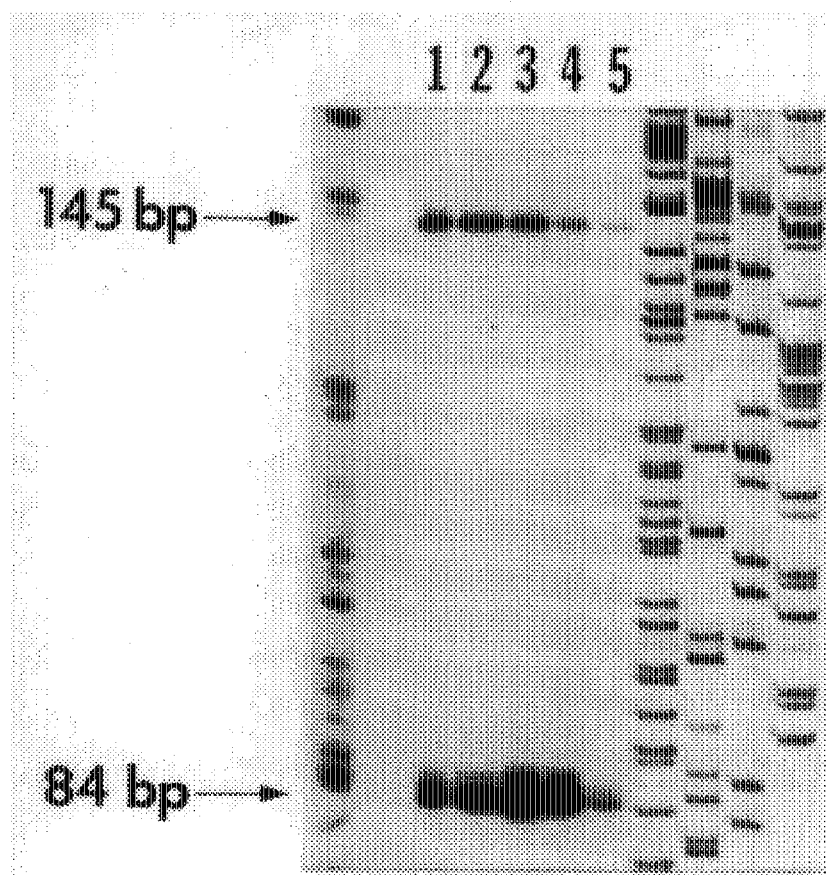
FIG. 1 shows a primer extension assay with an 84 nucleotide transcript and a 145 nucleotide transcript.

A manuscript entitled "The Cold-shock Response—"A Hot Topic" Jones and Inouye, *Molecular Microbiology*, 1994 (in press) (hereinafter "Hot Topic") co-filed herewith is incorporated herein by reference in its entirety and a second manuscript entitled "Family of the Major Cold-Shock Protein, CspA (CS7.4) of *Escherichia coli* Which Shows a High Sequence Similarity with the Eukaryotic Y-Box Binding Proteins", Lee et al. (in press) (hereinafter "Family") and the galley proof thereof are also co-filed herewith and incorporated by reference in their entirety. An untitled report including 7 Figures (hereinafter "Report") is also co-filed herewith and incorporated by reference in its entirety.

Publications of interest are listed under "References" are incorporated herein by reference. Those co-filed herewith are marked with an asterisk.

Studies carried out in conjunction with the invention have focused on the physiology of *E. coli* at low temperature with the initial discovery of the cold-shock response following the shift from 37° C. to 10° C. The cold-shock response describes a specific pattern of gene expression in response to downshift in temperature from the physiological growth temperature of the organism. This pattern includes the induction of a family of proteins called "cold-shock proteins" (Csp), continued synthesis of transcriptional and translational proteins despite the lag period, and specific repression of heat shock proteins.

The synthesis of individual proteins following a shift from 37° to 10° C. is shown on the autoradiograms of FIG. 9. Proteins whose differential rate of synthesis increased, i.e. the cold-shock proteins, are enclosed in boxes. Other proteins that were continuously synthesized, which include many transcriptional and translational proteins, are designated by arrows. Heat shock proteins DnaK and GroEL, whose synthesis was repressed are enclosed in circles. Jones et al. 1987, Jones et al. 1992a.

After the shift to 10° C., the response reaching maximum induction during the 3rd hour post shift followed by resumption of protein synthesis and growth after the 4th hour. The cold-shock response is induced with any 13° C. downshift or more. Generally, the magnitude of the induction is dependent upon the range of the temperature shift; the larger the range of the temperature shift, the more pronounced the response. Like the heat shock response, it is believed that the cold-shock response also serves an adaptive function.

The cold-shock response affects heat-shock proteins. It has been observed that a drop in temperature from physiological growth temperature to 13° C. is also characterized by a specific repression of heat-shock proteins (Jones et al. 1992). Repression of heat shock proteins has also been observed under conditions that cause both a decrease in the translational capacity of the cell and stimulation of ribosome formation, such as depriving streptomycin from a streptomycin-dependent mutant, or adding tetracycline to a partially tetracycline-resistant strain, or following a nutritional shift-up (Schnier, 1987). Other similar conditions that cause a decrease in the translational capacity and an increase in ribosomal protein synthesis, such as the addition of chloramphenicol or tetracycline to sensitive strains of *E. coli*, resulted in the induction of cold-shock proteins as well as repression of heat shock proteins in eukaryotes (VanBogelen & Neidhardt, 1990).

Stress-induced i.e. cold and heat shock induced proteins have also been identified whose expression is increased after a shift from physiological growth temperature to about 10° C. These proteins, namely protein TIP1 have been described (Kondo and Inouye, 1991; Kowalski et al., 1993). Another identified cold-shock gene encodes a nucleolin-like protein called NSR1 (Kondo and Inouye, 1992). Since these and other proteins can be induced by various stimuli, they often are referred to as "stimuli"-induced.

Studies carried out in conjunction with the invention suggest that the state of the ribosome is the physiological center for the induction of the cold-shock response (VanBogelen and Neidhardt, 1990). Consistent with the proposed involvement of the (p)ppGPP level in the cold-shock response is the finding that many of the inhibitors of translation that induce the cold-shock response also result in a decrease in the (p)ppGpp level (Lund and Kjeldgaard, 1972). The prevailing model is that an abrupt downshift in temperature causes a physiological state where the translational capacity of the cell is insufficient relative to the supply of charged tRNA signalling a decrease in the (p)ppGpp level and the induction of the cold-shock response (Jones et al., 1992a). The observation that an inhibitor of initiation of translation is an inducer of the cold-shock response (Jones et al., 1992a) combined with the finding that low temperature inhibits initiation of translation (Friedman et al., 1971, Broeze et al., 1978) suggest that a partial block in initiation of translation may be responsible for the decreased translational capacity following a downshift in temperature (Jones et al., 1992a). The function of the cold-shock response is not known. A plausible function may be to overcome the partial block in translation, thereby increasing the translational capacity of the cell or vice versa.

A Family of Stress-Induced Proteins

A family of stress-induced proteins has been identified which is characterized by highly conserved common domains of amino acid sequences. FIG. 10 shows the comparison of the amino acid sequences of four cold-shock proteins: CspA, CspB, CspC and CspD deduced from the DNA sequences of their genes, Seq. ID Nos. 7, 2, 4, and 10, respectively. A first domain includes the sequence VKWFN, Seq. ID No. 18. A second domain includes sequence K/NGF/YGFI. A third smaller domain includes sequence DV/IFV/AH and a forth domain which includes sequence E/DG/N/QE. The amino acid sequences of these four proteins are compared with the sequences of another cold-shock protein, cspB of *Bacillus subtilis*, and of two additional proteins, SC7.0 of *S. clavuligerus*, and YB1 of *H. sapiens*.

Figure 6:
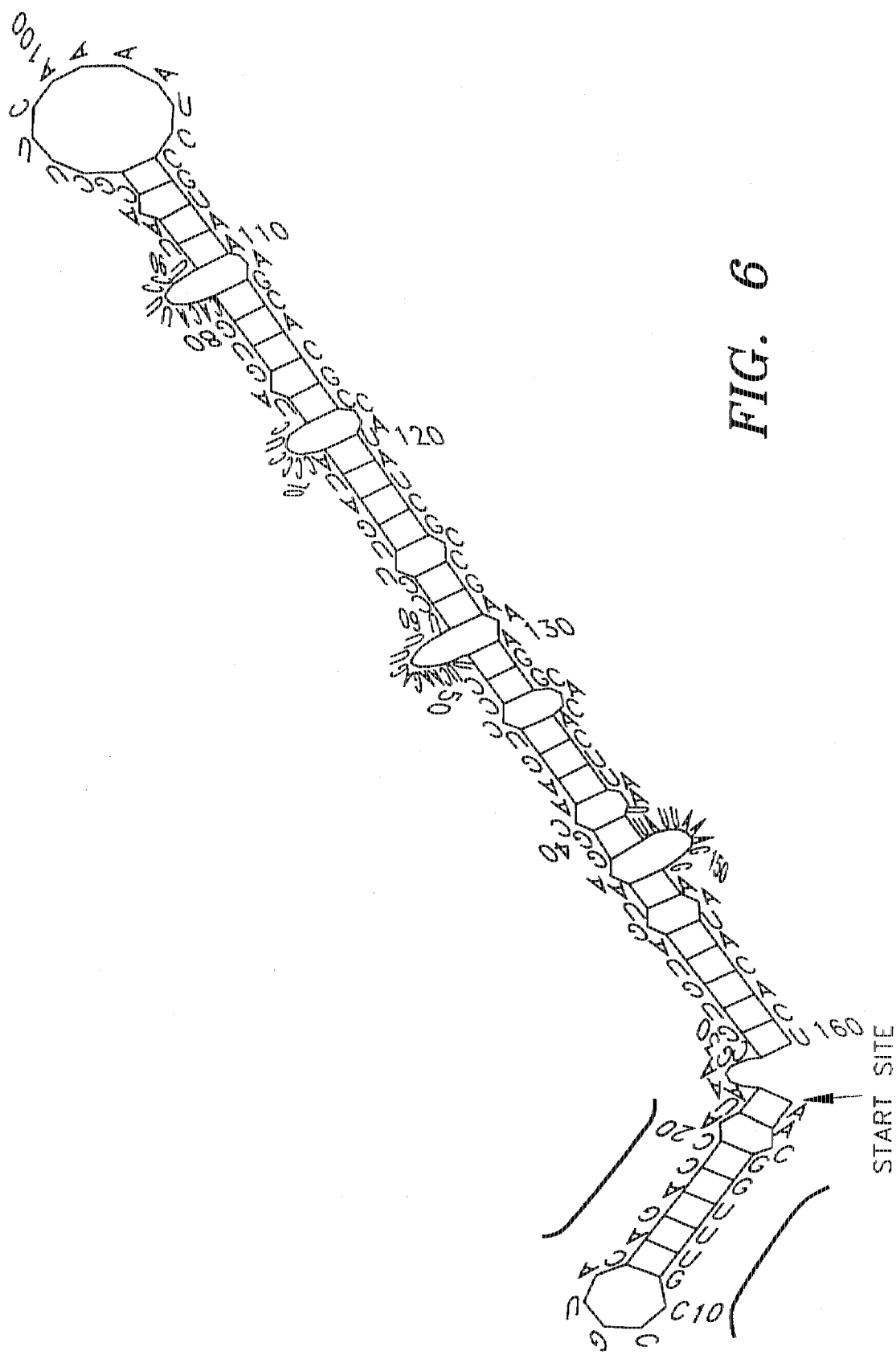
FIG. 6 shows the sequence of the –35 and –10 promoter regions of CspA and CspB compared with a consensus sequence of the transcription start signal of a prokaryote. Note the −35 similar domain.

FIG. 6 in the parent applicaton Ser. No. 07/852,013 and FIGS. 11 and 12 (Seq. ID Nos. 1 and 3) herein show the DNA sequence of CspA, CSpB, CspC and the respective amino acid sequences deduced from the DNA sequences, respectively.

All proteins have a very high content of aromatic amino acids: two (WF) in the first domain; two (FF) in the second domain; and one (F) in the third domain. Further, it will be observed from FIG. 10 that the content of aromatic acids of the proteins shown is: 8 residues (6 Phe, 1 Tyr and 1 Trp) for CSpA; 9 residues (7 Phe, 1Tyr and 1Trp) for CspB; 8 residues (7 Phe, 0 Tyr, and 1Trp) for CspC; and 8 residues (5 Phe, 2 Tyr and 1 Trp) for CspD. All 8 aromatic residues in CspA are conserved in all Csp proteins except for Phe-34 and Try-42 which are substituted with Tyr in CspD and Phe in CspC, respectively.

All Csp proteins contain only one conserved histidine residue (His-33 in CspA; except for CspD which contains 3). CspA, CspB, and CspC contain no cysteine residue, while CspD contains only one. All Csp proteins contain large numbers of charged residues: 16 (7 Lys, 0 Arg, 1 His, 2 Glu and 6 Asp) for CSpA; 15 (6 Lys, 1Arg, 1 His, 2 Glu and 5 Asp) for CspB; 15 (7 Lys, 0 Arg, 1 His, 4 Glu and 3 Asp) for CspC; and 17 (5 Lys, 1Arg, 3 His, 5 Glu and 3 Asp) for CspD.

It is noteworthy that the sequence identities are higher in the amino terminal half than in the carboxyl-terminal half of the amino acid sequence. In the amino terminal half, there are found two highly and large conserved sequences, K/NGF/YGFI and DV/IFV/AH.

CSDA, CspB, CspC and CspD encode a polypeptide of 70, 71, 69 and 74 amino acid residues, respectively. CspB (Seq. ID No. 2) has 56 identical residues to CpsA (79% identity); CspC (Seq. ID No. 4) has 48 identical to CspA (Seq. ID No. 7) (70% identity), and CspD (Seq. ID No:10) has 33 identical residues to CspA (45% identity). The percentage identity can also be computed by omitting the carboxyl-terminal extra residues of CspD as being outside the cold-shock domain as defined by CspA.

It is conceivable that amino acids of similar structures be interchangeable, for instance, Val by Ile or Leu; or Ser by Thr, and that aromatic amino acids be interchangeable with other aromatic amino acids, for instance, possibly Phe by Tyr, and aliphatic amino acids by other aliphatic amino acids. It is conceivable also that in the conserved domain(s), odd amino acid(s) can be replaced by one or more amino acids to make the domain fully or closer to fully homologous, for instance in the third domain Ile or Ala by Val or in the fifth domain, Ala or Asn by Glu or Gly.

By synthesis of these proteins or by appropriate substitution(s) in the nucleic acid sequences therefor, this can be readily performed so that any one of these proteins can be made the functionally equivalent or closer to another.

These unique features of these Csp proteins are likely to play important roles in the function and utility of these proteins. Individual Csp proteins can form dimers. Accordingly, it is believed that various heterodimers may be formed between different Cps proteins, which can be important for functional versatility of Csp proteins. Further, as discussed, CspA contains aromatic (and basic) residues. See in FIG. 10: K10, W11, K16, F18, F20, F31, H33, F34 and K60. It is possible that the aromatic residues that are found on the surfaces of the proteins play a role in the function of the Csps and, in particular in their interaction with their targets. The three dimensional structures of CspA determined by x-ray crystallography and NMR spectroscopy indicate that the protein comprises five antiparallel b-sheet structures, and that aromatic residues exposed on the surface of the protein interact with single-stranded DNA.

The Csps are believed to have the capacity to interact with ssDNA or RNA, possibly to unwind the secondary structures of these molecules and stabilize their primary structures. The Csp proteins have been reported to contain the RNA binding RNP1 sequence motif, [G-A]-[F-Y]-[G-A]-[F-Y]-[IVA]. Lansdman, 1992. Further, a putative ATP-dependent helicase is induced upon cold-shock, suggesting a specific requirement for "RNA chaperons" at low temperature. Further, it has been demonstrated that CspA recognizes a specific DNA sequence. Jones et al. 1992b. Csp proteins thus may be essential for the transcriptional machinery at low temperature in such a way to convert the closed DNA or RNA complex to an open complex during initiation of transcription. Another possible function of Csp proteins is their involvement in masking group of mRNAs to inhibit their translation.

Other uses for the members of the Csp family include the staining of DNA. The property of members of the Csp family to bind DNA and RNA indicate the potential use of these proteins in visualization of DNA in agarose and acrylamide gels. Standard procedures include the use of carcinogenic stains such as ethidium bromide. Members of the Csp family complexed with a fluorescent dye can potentially be used to safely stain DNA. The proteins can also be useful in the stabilization of DNA and RNA. The ability of the proteins to stabilize the primary structure of RNA and DNA indicate the potential use of these proteins in increasing the efficiency of DNA and RNA in various in vitro reactions. Also, these proteins can act as denaturases. Their property to unwind secondary structure in RNA or DNA indicate the potential use of these proteins to denature DNA irrespective of temperature.

The Csp proteins therefore can be seen to have very important potential commercial uses.

Promoters

The promoter of the invention is believed to be located on the cloned HindIII fragment between nucleotides 1 and 605. The first 997 bp of the cloned HindIII fragment contains all the necessary elements of the functional gene for regulated expression including the ribosome binding sites.

There is evidence of a promoter sequence at −35 and −10 upstream of the coding region, at positions 330 and 355, respectively. Another characteristic of the promoter is that it responds to a drop in temperature.

The promoter of the invention is activated at reduced temperature and directs transcription of the gene of the invention.

The promoter of the invention is cold-inducible in vivo and is recognized in vivo by RNA polymerase.

Parent patent application Ser. No. 07/852,013 which is incorporated herein by reference describes the cold-induced promoter for CspA. The −10 and −35 regions CTTATT and TTGCAT of the promoter sequence are shown in FIG. 6B of that application. The promoter was shown to control the expression of β-galactosidase. A plasmid (pKM005) carrying the lacZ gene without promoter was compared with the plasmid carrying the CspA promoter on a 806 bp HindIII-PvuII fragment. The induction by temperature shift from 37° C. to 15° C. and to 10° C. showed a significant increase (64%) in β-galactoside expression from *E. coli* cells harboring the plasmid carrying the CspA promoter.

In the above-described embodiment of the invention, the cspA promoter of the invention has been used in a classic model to control the expression of β-galactosidase. For this purpose, a plasmid (pKM005) containing the lac Z structural gene without promoter was compared with the plasmid containing the cspA promoter on an 806 bp HindIII-PvuII fragment (pJJG04).

A second plasmid, pJJG08, was constructed which contains a smaller nucleotide fraction of the upstream region of the cspA gene, terminating at the ApaLI site (bp 534). The results are shown in Table I.

TABLE I

| RESULTS OF EXPRESSION IN LAC STRAIN | | | |
|---|---|---|---|
| | TEMPERATURE | AFTER SHIFT | AFTER SHIFT |
| Plasmid | 37° | to 15° | to 10° |
| pKM005 | 6.7 | 4.1 | 3.7 |
| pJJG04 | 549.0 | 900.0 | 851.0 |
| pJJG08 | 40.7 | 45.6 | 56.1 |

Temperature are in °C.; other numerals refer to "Units" of enzyme activity.

The results show that the cspA promoter is capable of directing a heterologous gene to express a selected protein.

Likewise, all other Csp genes were studies for their ability to express β-galactosidase. All Csp genes tested were fused in the coding regions with the lacZ gene, and the expression of β-galactosidase was examined for these hybrid genes upon cold-shock. The plasmids were transformed into *E. coli*.

Cold-shock induction was observed for CspB as for CspA. Curiously, not for CspC and not for CspD. It is postulated that induction of these genes is stress-induced.

FIG. 6 shows the respective β-galactosidase activities (assayed according to Miller (1972)) expressed as ratios of the β-galactosidase activity at 15° C. to that at 37° C. The activities at 0 time were 33, 65, 424 and 16 units for CspA, CspB, CspC and CspD, respectively. The activity of CspC is particularly noteworthy.

The construction of lacZ fusion with Csp genes proceeded as follows. To construct the fusion gene the following fragments were first amplified by polymerase chain reaction (PCR) for each Csp gene; from nucleotide 1 to 655 for CspA (Goldstein et al., 1990), from nucleotide 1 to 566 for CspB (FIG. 5) Seq. ID No. 1, from nucleotide 1 to 721 for CspC (FIG. 5a) Seq. ID No. 3 and from nucleotide –696 to –330 for CspD (Gottesman et al., 1990). In the PCR reaction, both primers were designed to contain a BamHI site. In particular, the downstream BamHI sites for all Csp genes were designed to be created at the 11th codon of the Csp open-reading frames so that the first 10 amino acid sequences were fused in phase to the lacZ coding region at codon 7 at the BamHI site of the pRS414 vector (Simons et al., 1987). The plasmids were transformed in *E. coli* SG480. β-galactosidase activity was assayed according to Miller (1972).

To investigate possible differences between CspA and CspB, and whether CspB is also transcriptionally regulated, time course primer extension experiments were performed. Cell cultures were grown at 37° C. to early logarithmic phase and then transferred to 15° C. Prior to shifting the culture to 15° C., an aliquot was removed and designated as time 0 sample of the time course. Samples were subsequently removed at 10, 45, 75 and 120 minutes. Total RNA was isolated from each culture and subjected to primer extension using a radiolabeled oligonucleotide that hybridizes to the 5' untranslated region of the CspB gene. Inspection of the primer extension assay revealed two products, an 84 nucleotide transcript and a 145 nucleotide transcript (FIG. 1A, lane 1). Interestingly, the levels of the 84 nucleotide mRNA dramatically increased during the cold-shock treatment, peaking at 45 to 75 minutes and finally declining by 120 minutes. In contrast, the 145 nucleotide product appeared to linearly decrease upon shift to 15° C. Thus, this analysis suggests that the CspB gene contains two transcription start sites; one which appears stimulated by cold-shock treatment and a second which is repressed under the same conditions. See FIG. 5 which shows the cold-shock inducible promoter region, the cold-shock repressed promoter region and three transcription start sites. Functionally equivalent promoters are stress—in particular cold—induced are considered within the scope of the invention.

Figure 2:
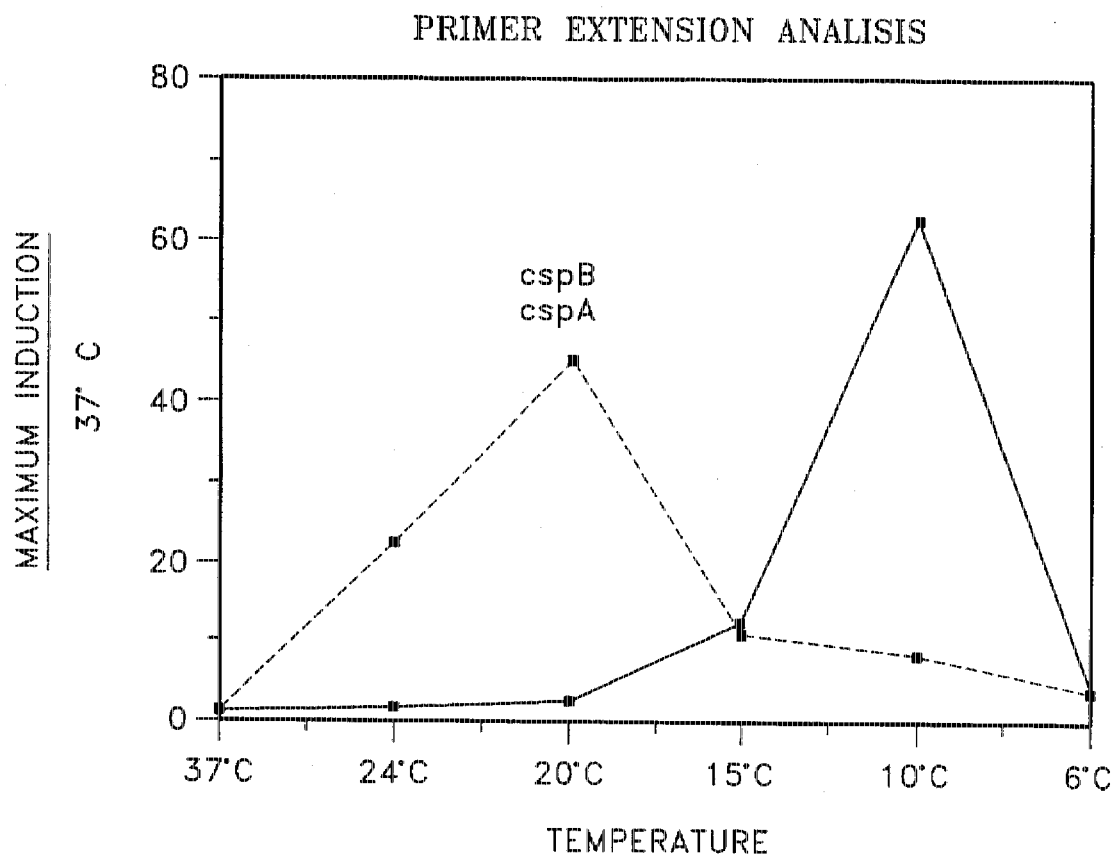
FIG. 2 shows exponentially growing cultures of *E. coli* at different temperatures.

To investigate why two highly homologous proteins, CspA and CspB, appear to have redundant reactions to cold-shock treatment, primer extension analysis was extended to include shifts from 37° C. to various lower temperatures. Cell cultures were grown at 37° C., shifted to 24° C., 20° C., 15° C., 10° C., or 6° C. and samples collected. Total RNA was harvested for each point during the time course for each independent temperature shift (i.e. 24° C., 20° C., 15° C., 10° C. or 6° C.) and the fold induction was expressed as a ratio between the maximum induction at each cold-shock temperature and that observed at 37° C. Interestingly, it was observed that induction of CspA peaked at 20° C. whereas CspB expression peaked at 10° C. (FIG. 2). Thus, the expression of the CspA and CspB genes is differentially regulated at different temperatures, suggesting that *E. coli* may have a mechanism for detecting temperature variations and responding by regulating gene expression levels.

Figure 3:
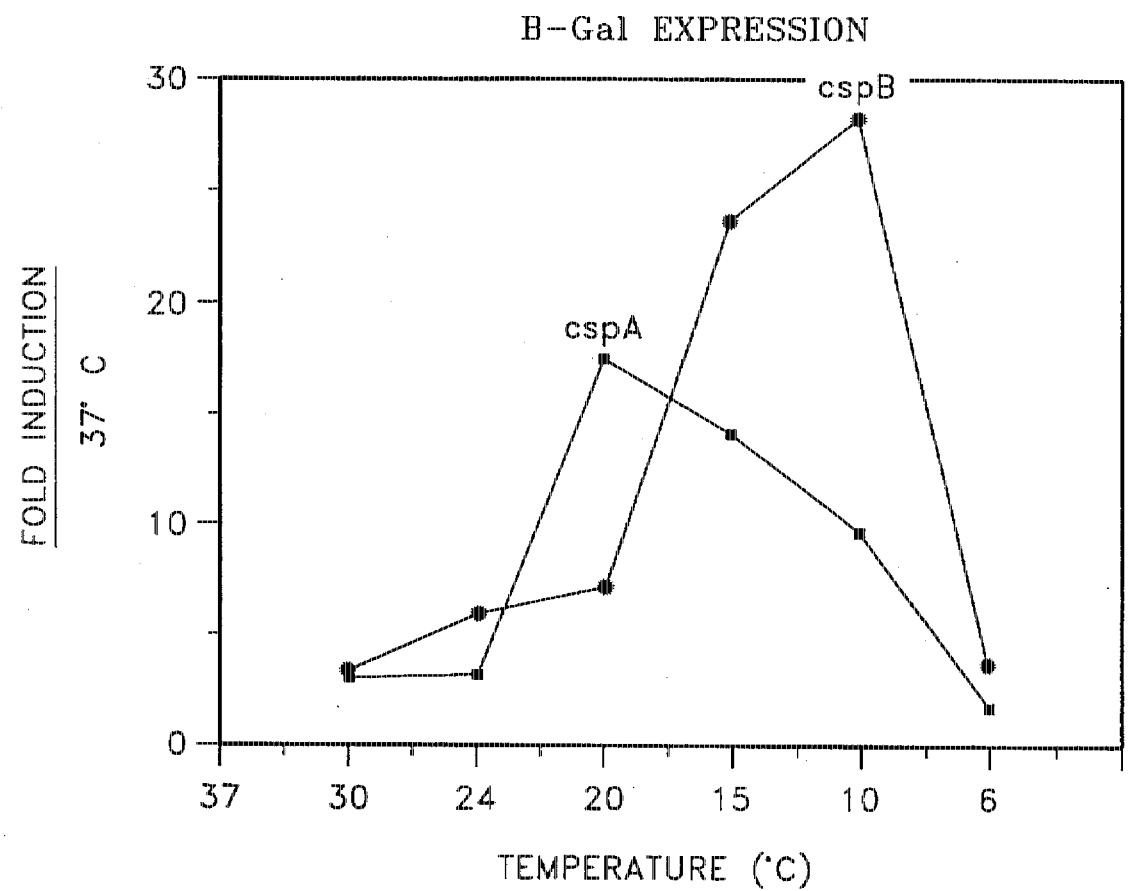
FIG. 3 shows lacZ translation fusions of CspA and CspB.

To investigate this possibility, and to determine whether the pattern of CspA and CSpB mRNA induction agrees with the pattern of protein production after cold-shock treatment at different temperatures, lacZ translation fusions of CspA and CspB were constructed (Li et al., 1994). β-galactosidase expression levels from the CspA and CspB promoters were consistent with the mRNA levels observed by primer extension at different temperatures (FIG. 3). Therefore, a linear correlation between the amount of CspA and CspB mRNA and their corresponding protein productions exist during cold-shock induction.

This result strongly suggests that although CspA and CspB are highly homologous genes and are both regulated at the level of transcription they have different gene expression patterns. This implies the existence of a thermoregulation system in *E. coli* which can adapt to low temperatures.

Figure 4:
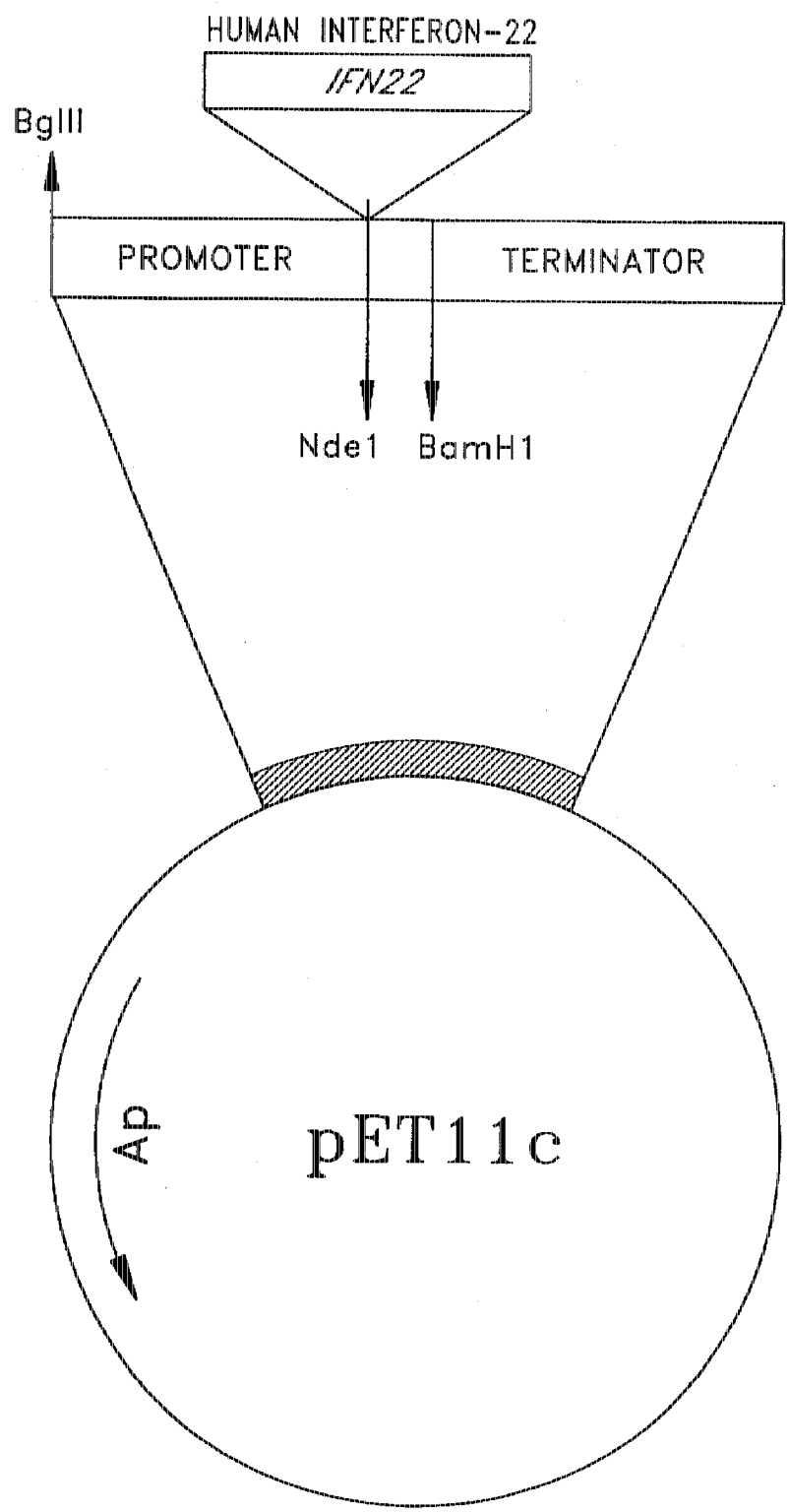
FIG. 4 shows a cold-shock vector which carries the promoter of CspA and CspB, respectively.

The promoters of CspA and CspB are effective to drive the expression of genes other than β-galactosidase. A "cold-shock" vector pET11c was constructed in which the T7 promoter was replaced by the CspA promoter and CspB, respectively driving the expression of the gene for human interferon α-2, which has been shown to be soluble at higher temperature. FIG. 4 shows the construction of the vector.

It is evident that the promoters of the Csp proteins like CspA and CspB are useful to control the expression of target genes to express proteins at temperatures below the normal physiological growth temperatures for the organism selected to express the target protein, whether a prokaryote or an eukaryote, like yeast. This is of particular interest in cases where the target protein has a tendency to become physiologically or biologically inactive (partly or totally) for any of several reasons. For instance, the protein may be susceptible to enzymatic denaturation (e.g. proteolytic) at physiological temperature or the target protein may be improperly folded to a physiologically inactive (or less active) configuration at physiological growth temperature.

The promoters which are induced otherwise than by cold-shock, like Cps C and CspD are useful to direct the synthesis of large amounts of mRNA corresponding to the target gene. The promoters described herein form therefore a family of promoters useful in numerous applications in which promoters are useful. See, *Current Protocols*, in Molecular Biology, Ausbel et al., Unit 16.

DETAILED FIGURE LEGENDS

FIGS. 1, 2, 3, 5, 5A and 6 are described herein in the text.

FIG. 4 Construction of Cold-shock Vector

To construct the cold-shock vector, the following fragments were first amplified by polymerase chain reaction (PCR) for each Csp gene; from nucleotide 1 to 616 for CspA gene, and from nucleotide 1 to 527 for CspB gene. Primers were designed such that a BgIII site was added at nucleotide 1 for CspA and for CspB; and a NdeI site at nucleotide 616 for CspA and at nucleotide 527 for CspB. Therefore, to construct the CspA cold-shock vector, the BgIII-NdeI fragment of vector pETIIc (ref. for pETRIIC-Studier, F. W. Rosenbert, A. H. Dunn, J. J. and Dubendoff, J. W. (1990) Methods Enzymol. 185, 60–89) was removed and replaced with the BgIII-NdeI fragment of CspA. To construct the CspB cold-shock vector, the BgIII-NdeI site of vector pETIIc. Therefore, to place expression of any gene under cold-shock regulation, the DNA fragment corresponding to the coding region is cloned at the NdeI or the bamHI site or the NdeI-BamHI site of the cold-shock vector.

Figure 8:
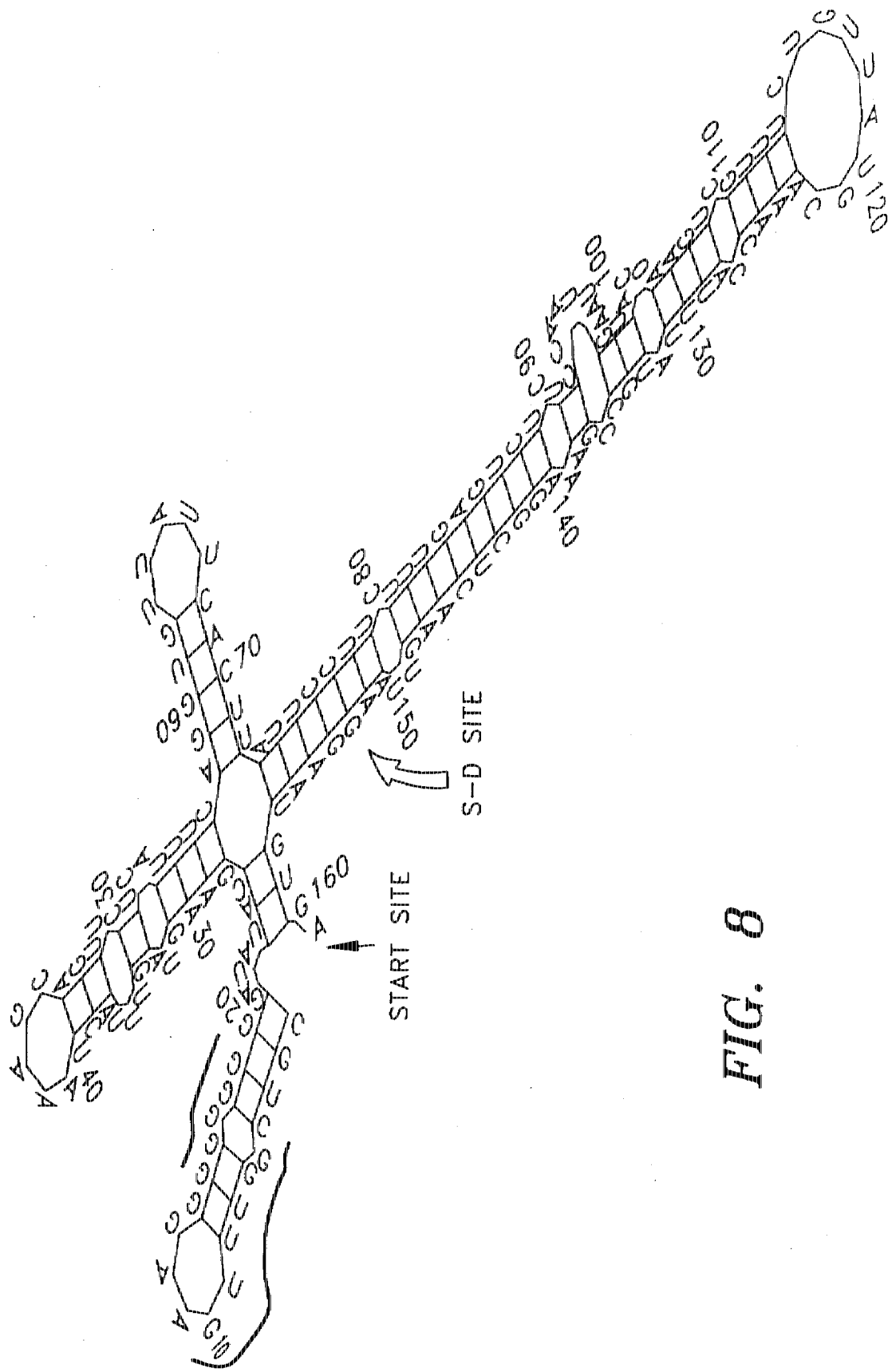
FIG. 8 shows the CspB leader region.
Figure 9A:
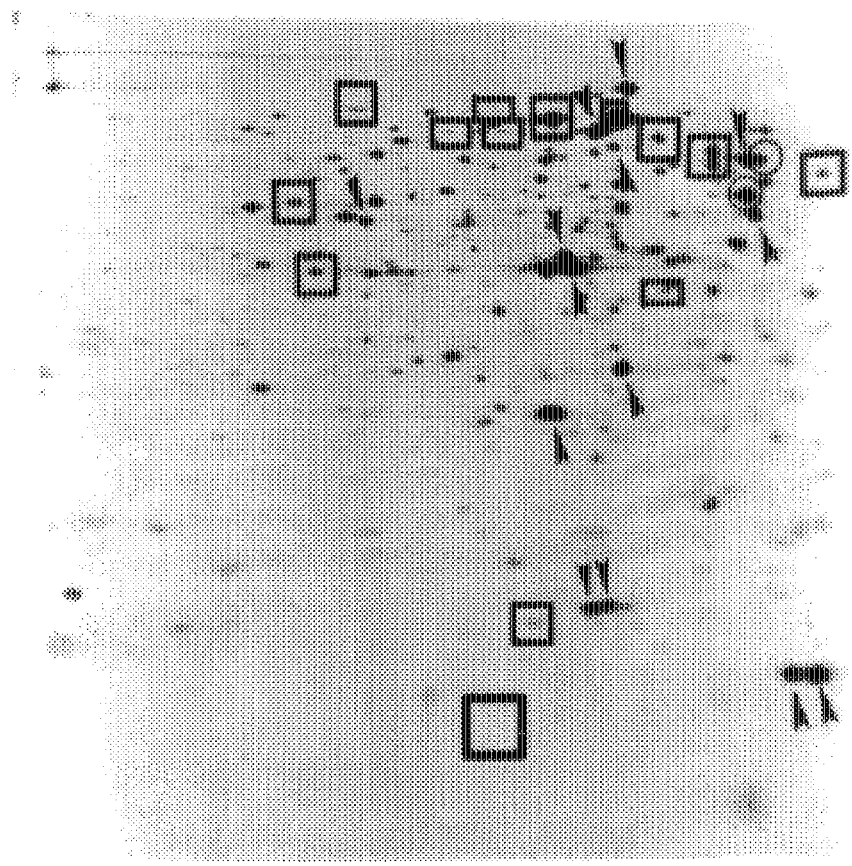
FIGS. 9A–9D show 4 autoradiograms made from two-dimensional gels of total gel extracts of individual protein cultures following a downward shift of temperature.
Figure 9B:
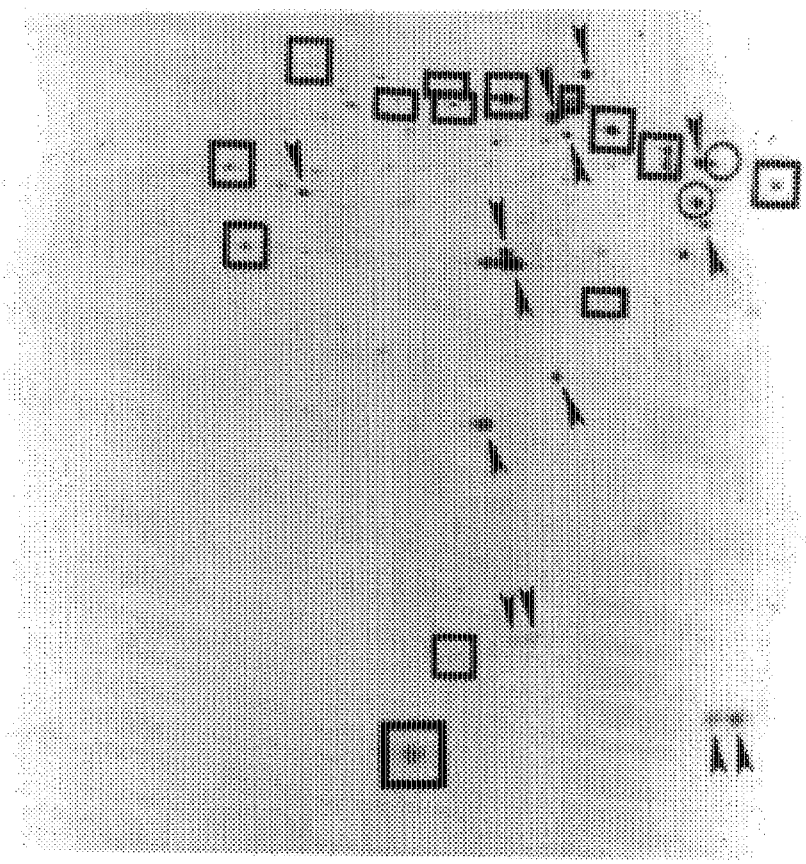
Figure 9C:
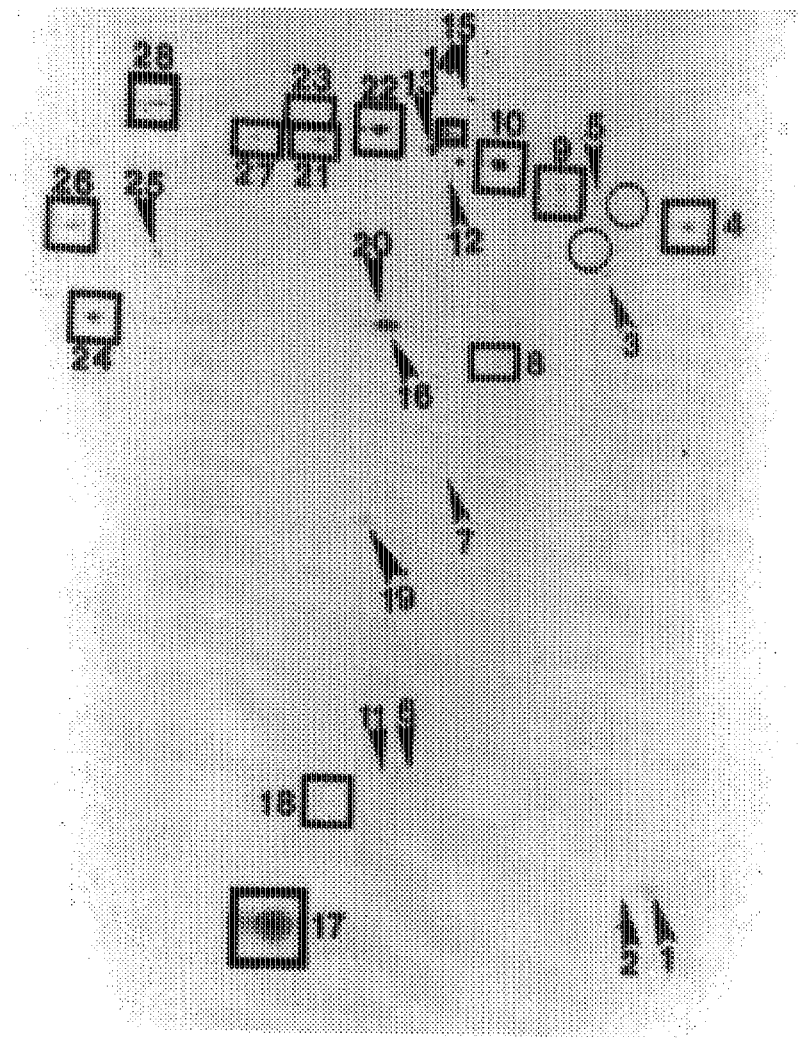
Figure 9D:
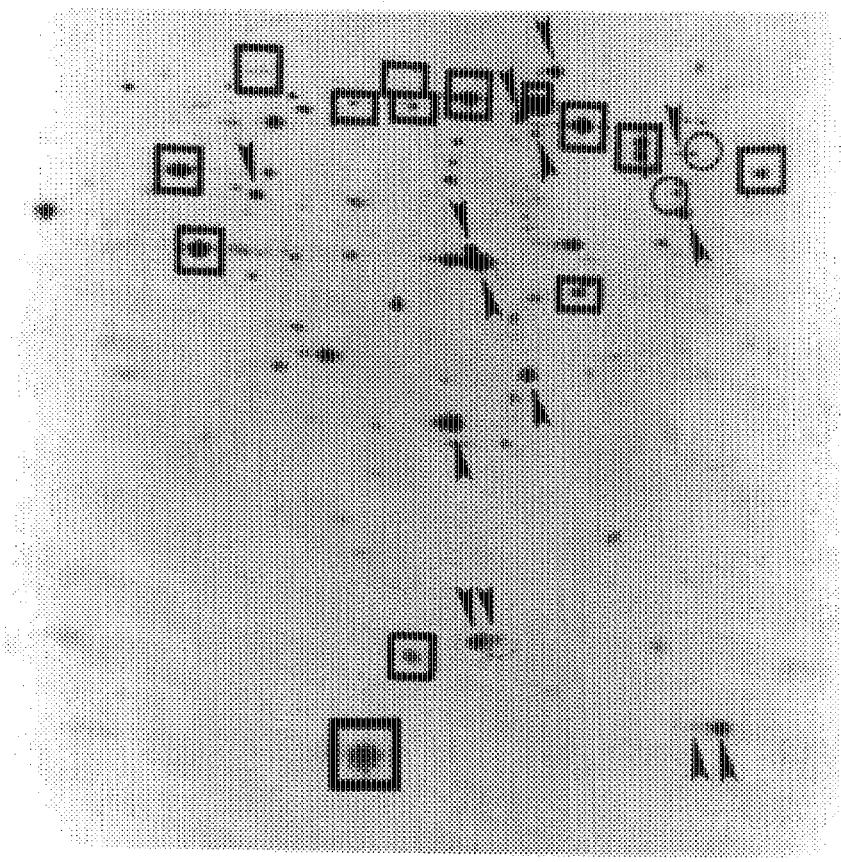

FIGS. 6 to 8 CspA Leader Region: (Sequence ID No. 5) Corresponds to the 5' untranslated region beginning at nucleotide position 457 (see CspA sequence) and ending at nucleotide position 616.

CspB Leader Region: (Sequence ID No. 6) corresponds to the 5' untranslated region beginning at nucleotide position 366 (see CspB sequence) and ending at nucleotide position 527.

The leader regions of CspA and CspB have the potential to form various stem loops which are very similar especially the first loop which has the following nucleotide sequences in common: CGGUUUGA and ACAGAC.

FIG. 9A–9D shows the synthesis of individual proteins following a shift from 37° to 10° C. The autoradiograms were made from two-dimensional gels of total cell extracts of cultures labeled with [35S] methionine before or at various times after the shift. (A) Labeled 5 min preshift. (B) Labeled 0 to 30 min postshift. (C) Labeled 120 to 150 min post shift. (D) Labeled 240 to 270 min postshift. Cellular extracts were prepared and applied to IEF tubes gels containing 1.6% pH 5–7 and 0.4% pH 3.5–10 ampholines and focused to equilibrium. The tube gels were then applied to sodium dodecyl sulphate/polyacrylamide (11.5%) second dimension gels. The numbered spots are the following polypeptides (Jones et al., 1987; La Teana et al., 1991; Jones et al., 1992b): 1, ribosomal protein L7; 2, ribosomal protein L12; 3, trigger factor; 4, NusA; 5, ribosomal protein S1; 6, ribosomal protein S6B; 7, EF-Ts; 8, RecA; 9, dihydrolipoamide acetyltransferase; 10, polynucleotide phosphorylase; 11, ribosomal protein S6A; 12, D74.0; 13, EF-G; 14, GyrA; 15, b-subunit of RNA polymerase; 16, EF-Tu; 17, CspA (F10.6); 18, H-NS; 19, F24.5; 20, F43.8; 21; F84.0; 22, pyruvate dehydrogenase-lipoamide; 23, initiation factor 2b; 24, G41.2; 25, G50.5; 26, G55.0; 27, G74.0; 28, initiation factor 2a. Proteins whose differential rate of synthesis increased, cold-shock proteins, are enclosed in boxes. Other proteins that were continually synthesized, which include many transcriptional and translational proteins, are designated by arrows. Heat shock proteins DnaK and GroEL, whose synthesis was repressed, are enclosed in circles.

FIG. 10 shows a comparison of *E. coli* CspA (Seq. ID No. 7) with other CspA-like proteins. The deduced amino acid sequence of CspA gene product of *E. coli* was compared with CspB (Seq. ID No. 2), CspC (Seq. ID No. 4), and CspD (Seq. ID No. 10) from *E. coli* (Lee et al., 1993); with CspB from *B. subtilis* (Seq. ID No. 13) (Willimsky et al., 1992); with SC7.0 from *S. calvuligerus* (Seq. ID No. 11) (Avgay et al., 1992); and with the "cold-shock domain" of YB1 from *H. sapiens* (Seq. ID No. 13) (Wistow, 1990; Wolffe et al., 1992).

FIG. 11 shows the nucleotide sequence and the deduced amino acid sequence of CspB (Seq. ID No. 1).

FIG. 12 shows the nucleotide sequence and the deduced amino acid sequence of CspC (Seq. ID No. 3).

Figure 13:
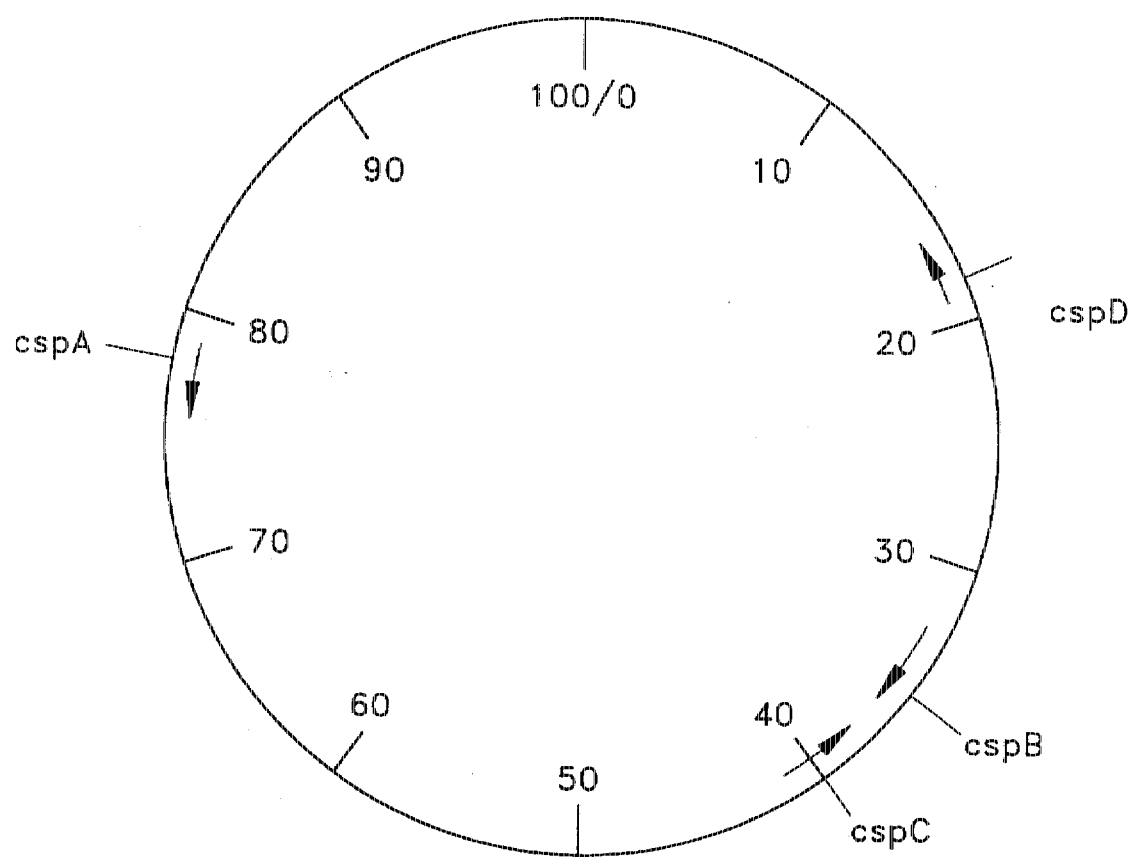
FIG. 13 shows chromosomal locations and the direction of transcription of Csp genes of *E. coli* based upon the location of Kohara's λ phages.

FIG. 13 shows the chromosomal locations and the direction of transcription of Csp genes of *E. coli* based upon the location of Kohara's λ phages.

Figure 14:
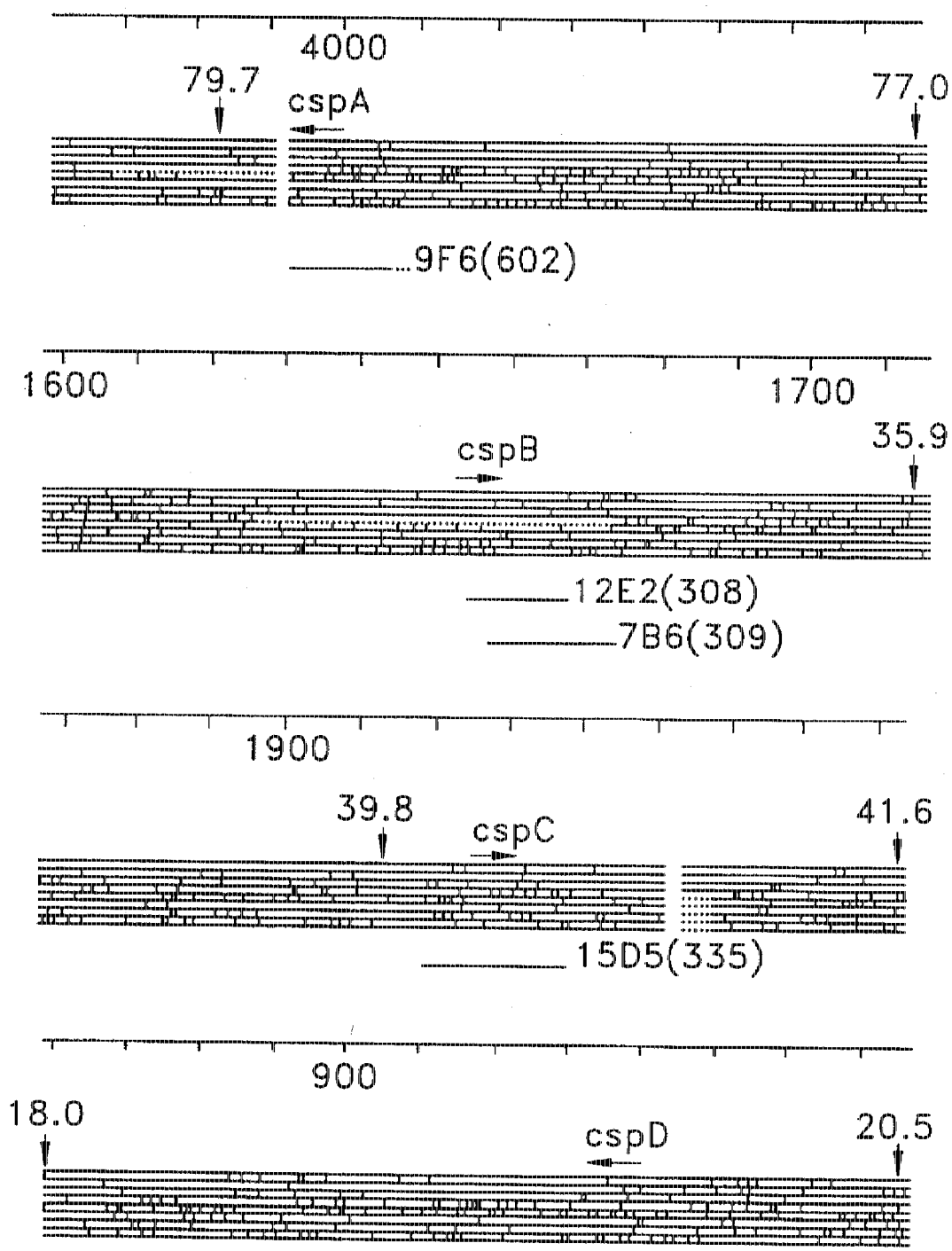
FIG. 14 shows the positions of Csp genes of *E. coli* on the Kohara restriction map (Kohara et al., 1987). The CspA gene was located on Kohara phage 9F6(602) (Goldstein et al., 1990). The CspB gene was located on Kohara phage 12E2 (308) and 7BC(309). The CspC gene was located on Kohara phage 15D5(335).

FIG. 14 shows the positions of Csp genes of *E. coli* on the Kohara restriction map (Kohara et al., 1987). The CspA gene was located on Kohara phage 9F6(602) (Goldstein et al., 1990). The CSpB gene was located on Kohara phage 12E2 (308) and 7BC(309). The CspC gene was located on Kohara phage 15D5(335).

Figure 15:
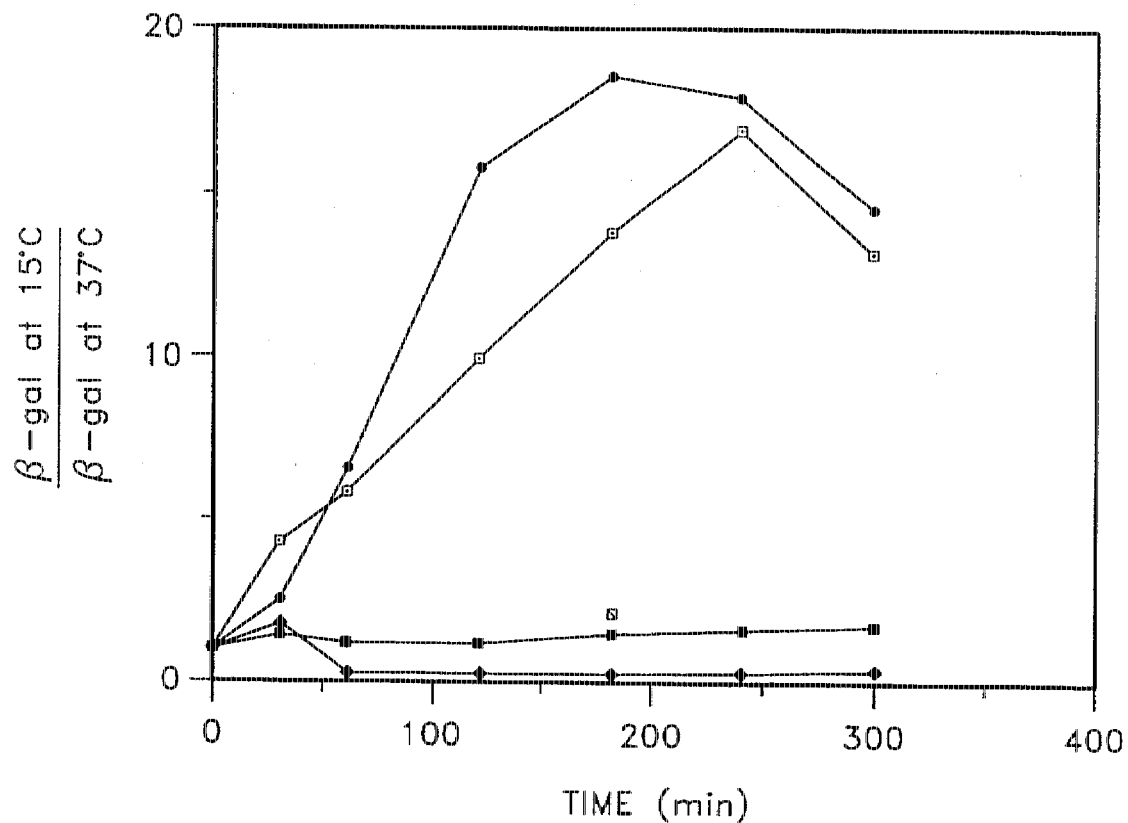
FIG. 15. shows β-galactosidase induction of Csp-lacZ translation fusions after temperature shift from 37° C. to 15° C. At a mid-exponential phase, cultures of *E. coli* SG480 harboring various plasmids grown at 37° C. in L broth were transferred to a incubator-shaker at 15° C. One-ml samples were taken at times indicated for the β-galactosidase assay (Miller, 1992).

FIG. 15 shows the β-galactosidase induction of Csp-lacZ Lranslation fusions after temperature shift from 37° C. to 15° C. At a mid-exponential phase, cultures of *E. coli* SG480 harboring various plasmids grown at 37° C. in L broth were transferee to a incubator-shaker at 15° C. One-ml samples were taken at times indicated for the β-galactosidase assay (Miller, 1992).

EXPERIMENTAL PROCEDURE AND TECHNIQUES

For the Experimental Protocols, see the co-filed manuscripts and publications which are incorporated herein by reference. DNA sequencing,protein purification were all performed by standard protocols. Also see, Tanabe et al. (1992) and references cited therein.

EXAMPLE 1

INDUCTION OF cs7.4

Cultures of *E. coli* SB221 (lpp hsdR trpE$^5$ lacy recA/F$^-$ lacI lac$^+$ pro$^+$) were grown to a density of approximately $2 \times 10^8$ cells/ml in a 10 ml culture volume prior to temperature shift. 1.1 ml aliquots of the cell culture growing at 30° C. were transferred to beakers at 42° C., 30° C., 25° C. and 18° C. containing 10 uCi of [$^{35}$S] methionine (Amersham Corp., >1000 Ci/mmol) or [$^{35}$S] Translabel (ICN Radiochemicals, Irvine, Calif.) and pulse-labeled for 10 minutes. All samples were collected by centrifugation and the pellets were dried by lyophilization. Samples were then subjected to sodium dodecyl sulfatepolyacryiamide gel electrophoresis (SDS-PAGE) on a 17.5% resolving gel. The gel was dried and exposed to X-ray film.

The resultant autoradiogram indicated a protein of 8 kdal apparent molecular weight produced only after shift to 25° C. No corresponding band was seen in the pre-shift or 43° C. shifted cultures. This protein is designated cs7.4.

EXAMPLE 4

USE OF csp PROMOTER TO DIRECT HETEROLOGOUS PROTEIN SYNTHESIS

The csp promoter was used to direct the synthesis of β-galactosidase in *E. coli* from the plasmid pJJG04. This plasmid was constructed as follows. The 2.4 kb HindIII fragment containing the gene was digested with PvuII. The resultant 806 bp fragment was separated on 0.8% agarose gel, the band excised and the DNA recovered by electroelution using a salt-bridge electroelution apparatus manufactured by IBI, Inc. as per manufacturer's instructions. This fragment was then ligated with T4 DNA ligase into the promoter-proving vector (pKM005 (Masui et al. ) after treatment of the vector fragment with XbaI restriction enzyme and Klenow fragment of DNA polymerass I. The *E. coli* lac deletion strain SB4288 was transformed and cells carrying the recombinant plasmid were selected as blue colonies on L-agar plates containing 50 ug/ml ampicillin and 40 mg/ml Xgal.

Cultures of *E. coli* SB4288 harboring plasmid pJJG04 were grown at 37° C. and shifted to 10° C. or 15° C. β-galactosidase activity before and after the shift using the substrate o-nitrophenyl-β-D-galactoside as described by Miller. The results indicate a 64% increase in β-galactosidase activity upon shift of the culture to 15° C., evidencing induction of transcription from the cloned cspA promoter and subsequent expression of β-galactosidase.

This example illustrates well the versatility of the promoter sequence oJ the invention.

EXAMPLE 5

EXPRESSION OF cs7.4 STRUCTURAL GENE AT 37° C.

The cspA structural gene was subcloned into a high level expression vector, pINIII (lpp$^{P5}$) using an XbaI site created just upstream of the structural gene using oligonucleotide directed site specific mutagenesis. Upon addition of IPTG, expression of the cs7.4 protein could be detected by SDS-PAGE analysis of whole cell lysates.

For vector that can be used to clone a DNA fragment carrying a promoter and to examine promoter efficacy, see Masui et al.

It is understood that other competent microorganism hosts (eucaryotic and procaryotic) can be transformed genetically in accordance with the invention. Bacteria which are susceptible to transformation, include members of the Enterobacteriaceae, such as *E. coli*, Salmonella; Bacillaceae, such as subtilis, Pneumococcus; Streptococcus; yeast strains and others.

Of particular interest may be the transformation of yeast cells, such as *Sacchdromyces cerevisiae* with the structural gene of the invention or of all or part of the nucleotide sequence shown in Sequence ID No. 6. Basic techniques of yeast genetics, appropriate yeast cloning and expression vectors and transformation protocols are discussed in *Current Protocols in Molecular Biology*, Supplement 5 (1989) which is specifically incorporated herein by reference.

Likewise, vertebrate cell cultures may be transformed with the structural gene of the invention or part thereof or with part or all of the nucleotide sequence shown in FIG. 6. One skilled in the art will select an appropriate cell culture as a COS-7 of monkey fibroblasts. Appropriate techniques for the transfection of DNA into eucaryotic cells are described in Current Protocols, Section 9 (also incorporated herein by reference). Illustrated protocols are shown to work well with such cell lines as HeLa, BLAB/c 3T3, NIH 3T3 and rat embryo fibroblasts.

Additional vectors and sources are listed in Perbal (22) (pages 277–296) including yeast cloning vectors, plant vectors, viral vectors, with scientific appropriate literature references, and cloning vectors from commercial sources.

Numerous suitable microorganisms are available from the American Type Culture Collection, 12301 Parklawn Drive, Rockville, Md., 20852-1776.

A number of embodiments have been illustrated herein. It is contemplated that one skilled in the art can readily make variations thereof without departing from the spirit and the scope of the invention.

REFERENCES

* Copy is filed herewith

1. Ang, D. et al. (1991) J. Biol Chem 266: 24233–24236.
2. Avgay, Y., Aharonowitz, Y., and Cohen, G. (1992) Streptomyces contain a 7.0 kDa cold shock like protein. Nucl. Acid. Res. 20:5478.
3. Broeze, R. J. et al. (1978) J. Bacteriol. 134: 861–874.
4. Cashel, M. and Rudd, K. E. (1987) The Stringent Response. In *Escherichia coli* and *Salmonella typhimurium*: cellular and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1410–1438.
5. Clouter, J. et al. (1992) Rhizobia. Appli. Envir. Microbiol. 58: 2846–2853.
6. Danyluk, J. et al. (1991) Biochem. Cell. Biol. 69: 383–391.
7. Deschamps, S., Viel, A., and leMaire, M. (1991) Purification----two thermostable components of messenger ribonucleoprotein particles (mRNPs) from Xenopus laevis oocytes, belonging to a novel class of RNA binding proteins. FEBS Lett. 282:110–114.
8. Didier, D. K., Schiffenbauer, J. Woulfe, S. L., Zacheis, M. J. and Schwartz, D. B. (1988) Characterization of the cDNA encoding a protein binding to the major histocompatibility complex class II Y-box. Proc. Natl. Acad. Sci. USA 85: 7322–7326.
9. Donovan, W. P., & Kushner, S. R. (1986) Proc. Natl. Acad. Sci. USA 86: 120–124.
10. Doniger, J., Landsman, D., Gonda, M. A., and Wistow, G. (1992) The product of unr, the highly conserved gene upstream of N-ras, contains multiple repeats similar to the cold-shock domain (CSD), a putative DNA-binding motif. The New Biologist 4: 389–395.
11. Dreyfuss, G. et al. (1993) Annu. Rev. Biochem. 62: 289–321.
12. Friedman, D. I. et al. (1984) Microbiol Rev. 48:299–325.
13. Friedman, H. et al. (1969) Nature 233: 909–913.
14. Friedman, H. et al. (1971) J. Mol. Biol. 61: 105–121.
15. Georgopoulos, C. (1992) Trends Biochem. Sci. 17: 295–299.
16. Gething, M. J. et al. (1992) Nature 355: 33–45.
*17. Goldstein, J., Pollitt, N. S., and Inouye, M. (1990) Major cold-shock protein of *Escherichia coli*. Proc. Natl. Acad. Sci. USA 87: 283–287.
18. Gottesman, S., Clark, W. P., and Maurizi, M. R. (1990) The ATP-dependent Clp protease of *Escherichia coli*. J. Biol. Chem. 265: 7886–7893.

19. Gross, C. A. et al. (1990) The function and regulation of heat shock proteins in *Escherichia coli*. In Stress Proteins in biology and medicine. Morimoto, R., Tissieres, A., Georgopoulos, C (eds). Cold Spring Harbor, N.Y.: Cold Spring Harbor Laboratory, pp. 166–190.
20. Grunberg-Manago, M. (1987) Regulation of the expression of aminoacyl-tRNA synthetases and translation factors. In *Escherichia coli* and *Salmonella typhimurium*: celluluar and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1386–1409.
21. Gualerzi, C. O., and Pon, C. L. (1990) Biochemistry 29: 5881–5889.
22. Herendeen, S. L. et al. (1979) J. Bacteriol. 139: 185–194.
*23. Jiang, W. et al. (1993) J. Bacteriol. 177: 6824–5828
*24. Jones, P. G., VanBogelen, R. A., and Neidhardt, F. C. (1987) Induction of proteins in response to low temperature in *Escherichia coli*. J. Bacteriol. 169: 2092–2095.
*25. Jones, P. G., et al. (1992a) J. Bacteriol. 174: 3903–3914.
*26. Jones, P. G. et al. (1992b) J. Bacteriol. 174: 5798–5802.
27. Julseth, C. R., and Inniss, W. E. (1990) Can. J. Microbiol. 36: 519–524.
28. Kohara, Y., Akiyama, K., and Isono, K. (1987) The physical map of the whole *E. coli* chromosome: Application of a new strategy for rapid analysis and sorting of a large genomic library. Cell 50: 495–508.
29. Kondo, K., and Inouye, M. (1991) J. Biol. Chem. 266: 1737–1744.
30. Kondo, K., and Inouye, M. (1992) J. Biol. Chem. 267: 16252–16258.
31. Kondo, K. et al. (1992) J. Biol Chem. 267: 16259–16265.
32. Kowalski, L. R. Z. et al. (1993) manuscript submitted.
33. Landsman, D. (1992) Nucleic Acids Res. 20: 2861–2864.
34. La Teana, A., et al. (1991) Proco Natl. Acad. Sci. USA 88: 10907–10911.
35. Lee, S. J. et al. (1993) manuscript submitted.
36. Lemaux, P. G. et al. (1978) Cell 13: 427–434.
37. Lopilato, J., Bortuer, S., and Beckwith, J. (1986) Mutations in a new chromosomal gene of *Escherichia coli* K-12, pcnB, reduced plasmid copy number of pBR322 and its derivatives. Mol. Gen Genet. 205: 285–290.
38. Lund, E., and Kjeldgaard, N. O. (1972) Eur. J. Biochem. 28: 316–326.
39. Mackow, E. R., and Chang, F. N. (1983) Mol. Gen. Genet. 192: 5–9.
40. Maniak, M., and Nellen, W. (1988) Mol. Cell. Biol. 8: 153–159.
41. Maniatis, T., Fritsch, E. F., and Sambrook, J. (1982) Molecular Cloning: A Laboratory Manual. Cold Spring Harbor Laboratory, Cold Spring Harbor, N.Y. Miller, J. H. (1972) Experiments in Molecular Genetics pp. 352–355, Cold Spring Harbor Laboratories, Cold Spring Harbor, N.Y.
42. Murray, M. T., Schiller, D. L. and Franke, W. W. (1992) Sequence analysis of cytoplasmic mRNA-binding proteins of Xenopus oocytes identifies a family of RNA binding proteins. Proc. Natl. Acad. Sci. USA 89: 11–15.
43. Namura, Y., and Mizusawa, S. (1985) EMBO J. 4: 527–532.
44. Neidhart, F. C., and VanBogelen, R. A. (1987) Heat Shock Response. In *Escherichia coli* and *Salmonella typhimurium*: celluluar and molecular biology. Neidhardt, F. C., Ingraham, J. L., Low, K. B., Magasanik, B., Schaechter, M. and Umbarger, H. E., (eds). Washington, D.C.: American Society for Microbiology, pp. 1334–1345.
45. Newkirk, K., et al. (1993) manuscript submitted.
46. Ng, H., et al. (1962) J. Bacteriol. 84: 331–339.
47. Niki, H., et al. (1991) EMBO J. 10: 183–193.
48. Pao, C. C., and Dyess, B. T. (1981) J. Biol. Chem. 256: 2252–2257.
49. Patterson, T. A., and Dean M. (1987) Preparation of high titer phage lysates. Nucl. Acids Res. 15: 6298.
50. Qoronfleh, M. W. et al. (1992) J. Bacteriol. 174: 7902–7909.
51. Ranjan, M., et al. (1993) Genes & Development 7: 1–12.
52. Roberts, M. E. and Inniss, W. E. (1992) Curr. Microbiol. 25: 275–278.
53. Salerno, G. L., and Pontis, H. G. (1988) Plant Physiol. 89: 648–651.
54. Sanger, F., Nicklen, S., and Coulsen, A. R. (1977) DNA sequencing with chain-terminating inhibitors. Proc. Natl. Acad. Sci. USA 74: 5463–5467.
*55. Schindelin, H., Marahiel, M. A., and Heinemann, U. (1993) Universal nucleic acid-binding domain revealed by crystal structure of the *B. subtilus* major cold-shock protein. Nature 364: 164–168.
56. Schindelin, H, Cordes, F., Jiang, W., Inouye, M., and Heinemann, U. (1993b) manuscript submitted.
*57. Schnuchel, A., Wiltscheck, R., Szisch, M., Herrler, M., Willimsky, G., Graumann, P., Marahiel, M. A., and Holak, T. A. (1993) Structure in solution of the major cold-shock protein from Bacillus subtilus. Nature 364: 169–171.
58. Schmid, M. B. (1990) Cell 63: 451–453.
59. Schnier, J. (1987) J. Gen. Microbiol. 133: 3151–3158.
60. Simons, R. W., Houman, F., and Kleckner, N. (1987) Improved single and multicopy lac-based cloning vectors for protein and operon fusions. Gene 53: 85–96.
61. Shaw, M. K., & Ingraham, J. L. (1965) J. Bacteriol. 90: 141–146.
62. Shaw, M. K., and Ingraham, J. L. (1967) J. Bacteriol. 94: 157–164.
63. Squires C., and Squires, C. (1992) J. Bacteriol. 174: 1081–1085.
64. Stanier R. Y. et al. (1976) The microbial world, 4th ed., Prentice-Hall, Inc., Englewood Cliffs, N.J.
65. Sugino, A. et al. (1977) Proc Natl Acad Sci USA 74: 4767–4771.
66. Tafuri, S. R., and Wolffe, A. P. (1990) Xenopus Y-box transcription factors: Molecular cloning, functional analysis, and developmental regulation. Proc. Natl. Acad. Sci. USA 87: 9028–9032.
67. Takata, R. T. et al. (1985) Nucleic Acids Res. 13: 7289–7296.
*68. Tanabe, H., Goldstein, J., Yang, M., and Inouye, M. (1992) Identification of the promoter region of the *Escherichia coli* major cold-shock gene, cspA. J. Bacteriol. 174: 3867–3873.
69. VanBogelen, R. A. and Neidhardt, F. C. (1990) Proc. Natl. Acad. Sci. USA 87: 5589–5593.
70. Vieira, J., and Messing, J. (1982) The pUC plasmids, and m14mp7-derived system for insertion mutagenesis and sequencing with synthetic universal primers. Gene 19: 259–268.
71. Walker, G. C. (1984) Microbial. Rev. 48: 60–93.
72. Westphal, M. et al. (1986) FEBS Lett 209: 92–96.
73. Willimsky, G., Bang, H., Fischer, G., and Marahiel, M. A. (1992) Characterization of cspB, a *Bacillus subtilis* inducible cold-shock gene affecting cell viability at low temperatures. J. Bacteriol. 174: 6326–6335.

74. Wistow, G. (1990) Nature 344: 823–824.
75. Wolffe, A. P., Tafuri, S., Ranjan, M., and Familari, M. (1992) The Y-box factors: A family of nucleic acid binding proteins conserved from Escherichia coli to man. New Biol. 4: 290–298.

---

We claim:

1. An isolated bacterial protein which comprises an amino acid sequence selected from the group consisting of DGSK, as shown in Seq. ID No. 14, and YRTL, as shown in Seq. ID No. 15, which protein is a member of the Csp family of proteins, wherein the protein is selected from the group consisting of CspA, as shown in Seq. ID No. 7, CspB of *Escherichia coli*, as shown in Seq. ID No. 2, CspC, as shown in Seq. ID No. 4, and CspD, as shown in Seq. ID No. 10.

2. The protein of claim 1 wherein the protein is CspA.

3. The protein of claim 1 wherein the protein is CspB of *Escherichia coli*.

\* \* \* \* \*